US011891415B2

(12) United States Patent
Hughes et al.

(10) Patent No.: US 11,891,415 B2
(45) Date of Patent: *Feb. 6, 2024

(54) DEPSIPEPTIDES AND USES THEREOF

(71) Applicant: NovoBiotic Pharmaceuticals, LLC, Cambridge, MA (US)

(72) Inventors: Dallas Hughes, Bolton, MA (US); Amy Spoering, Waltham, MA (US); Aaron J. Peoples, Somerville, MA (US); Losee Lucy Ling, Arlington, MA (US); Anthony Nitti, Lexington, MA (US); William Millett, Worcester, MA (US); Ashley Zullo, Cambridge, MA (US); Kim Lewis, Newton, MA (US); Slava Epstein, Dedham, MA (US); Alysha Desrosiers, Medford, MA (US); Catherine Achorn, Cambridge, MA (US); Kelly Demeo, Brookline, MA (US)

(73) Assignee: NovoBiotic Pharmaceuticals, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/524,230

(22) Filed: Nov. 11, 2021

(65) Prior Publication Data

US 2022/0185845 A1    Jun. 16, 2022

Related U.S. Application Data

(63) Continuation of application No. 16/500,470, filed as application No. PCT/US2018/025365 on Mar. 30, 2018, now Pat. No. 11,203,616.

(60) Provisional application No. 62/481,412, filed on Apr. 4, 2017.

(51) Int. Cl.
*C07K 11/02* (2006.01)
*A61P 31/04* (2006.01)
*C12N 1/20* (2006.01)
*A61K 38/00* (2006.01)

(52) U.S. Cl.
CPC ............. *C07K 11/02* (2013.01); *A61P 31/04* (2018.01); *C12N 1/20* (2013.01); *A61K 38/00* (2013.01)

(58) Field of Classification Search
CPC ............ C07K 11/02; C07K 7/06; C07K 7/56; A61P 31/04; C12N 1/20; A61K 38/00
See application file for complete search history.

(56) References Cited

U.S. PATENT DOCUMENTS 11,203,616 B2 * 12/2021 Hughes .................. C07K 11/02

FOREIGN PATENT DOCUMENTS

| CN | 101173004 A | 5/2008 |
| JP | 2016-505547 A | 2/2016 |
| TW | 201428004 A | 7/2014 |
| WO | 2014/089053 A1 | 6/2014 |
| WO | 2015/188140 A1 | 12/2015 |

OTHER PUBLICATIONS

Ling et al, Nature, Jan. 22, 2015, vol. 517, pp. 455-459 (Year: 2015).*
Abdel Monaim et al., Converting Teixobactin into a Cationic Antimicrobial Peptide (AMP). J Med Chem. Sep. 14, 2017;60(17):7476-7482.
Abdel Monaim et al., Re-evaluation of the N-terminal substitution and the D-residues of teixobactin. RSC Advances. Jul. 28, 2016;6(77):73827-9.
Parmar et al., Defining the molecular structure of teixobactin analogues and understanding their role in antibacterial activities. Chem Commun (Camb). Feb. 7, 2017;53(12):2016-2019.
Shoji et al., Isolation and characterization of hypeptin from *Pseudomonas* sp. J Antibiot (Tokyo). Oct. 1989;42(10):1460-4.
Yang et al., X-ray crystallographic structure of a teixobactin analogue reveals key interactions of the teixobactin pharmacophore. Chem Commun (Camb). Feb. 28, 2017;53(18):2772-2775.
International Search Report and Written Opinion for Application No. PCT/US2018/025365, dated May 24, 2018, 11 pages.
Von Nussbaum et al., Multiple attack on bacteria by the new antibiotic teixobactin. Angew Chem Int Ed Engl. Jun. 1, 2015;54(23):6684-6.
Yang et al., Elucidation of the Teixobactin Pharmacophore. ACS Chem Biol. Jul. 15, 2016;11(7):1823-6.
U.S. Appl. No. 16/500,470, filed Oct. 3, 2019, U.S. Pat. No. 11,203,616, Issued.

* cited by examiner

*Primary Examiner* — Sudhakar Katakam
(74) *Attorney, Agent, or Firm* — McCarter & English, LLP; Maria Laccotripe Zacharakis; Yelena Margolin

(57) ABSTRACT

The present invention relates generally to novel depsipeptides, to methods for the preparation of the novel depsipeptides, to pharmaceutical compositions comprising the novel depsipeptides; and to methods of using the novel depsipeptides to treat or inhibit various disorders.

20 Claims, 1 Drawing Sheet

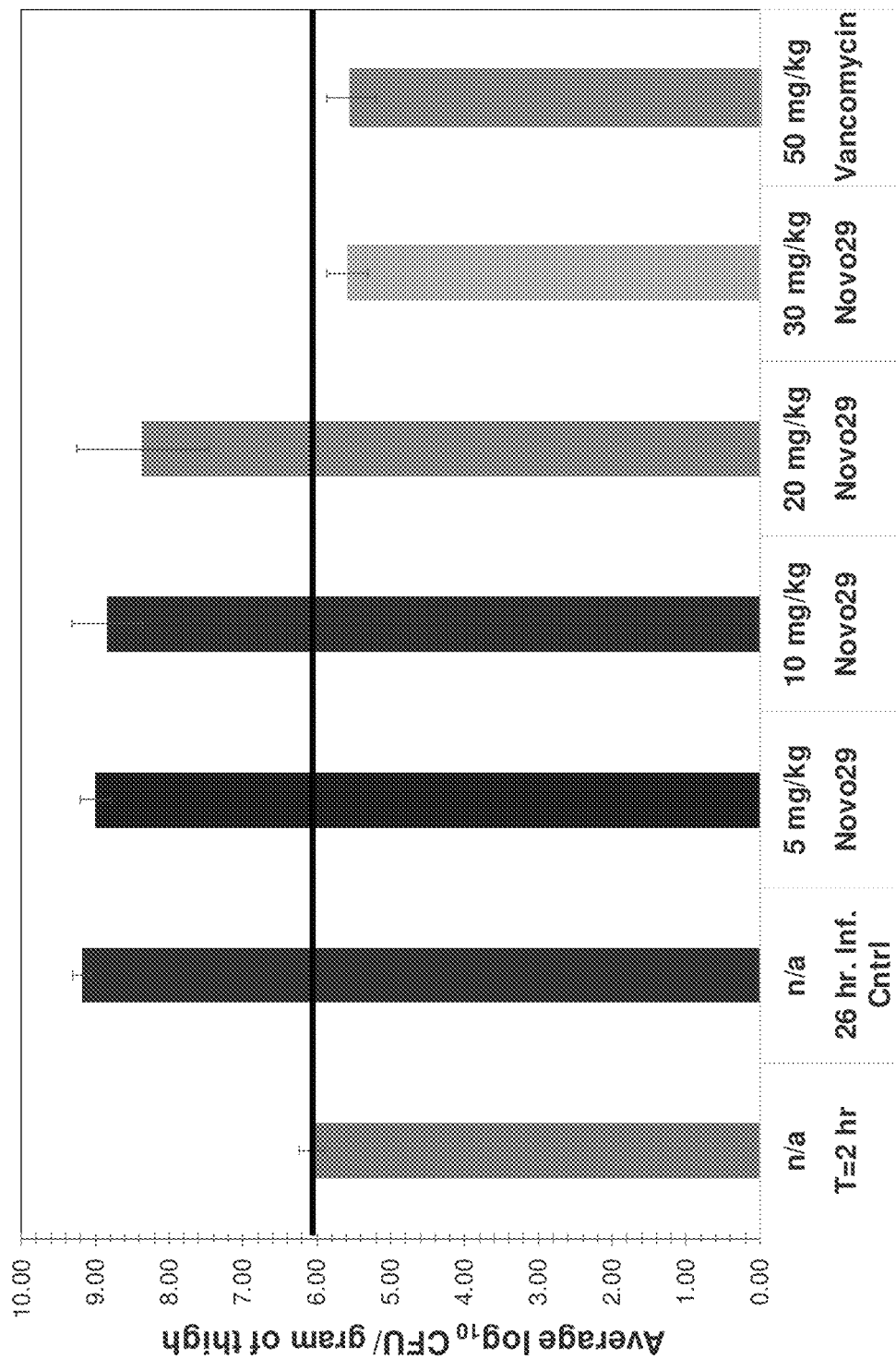

DEPSIPEPTIDES AND USES THEREOF

RELATED APPLICATIONS

This application is a continuation of U.S. application Ser. No. 16/500,470, filed on Oct. 3, 2019; which is a 35 U.S.C. § 371 national stage filing of International Application No. PCT/US2018/025365, filed on Mar. 30, 2018; which claims the benefit of priority to U.S. Provisional Application No. 62/481,412, filed on Apr. 4, 2017. The entire contents of each of the foregoing applications are hereby incorporated herein by reference.

GOVERNMENT SUPPORT

This invention was made with Government support under Grant No. R43AI136137-03 and R44AI091224-03 awarded by the National Institutes of Health. The Government has certain rights in the invention.

BACKGROUND OF THE INVENTION

Among modern medicine's great achievements is the development and successful use of antimicrobials against disease-causing microbes. Antimicrobials have saved numerous lives and reduced the complications of many diseases and infections. However, the currently available antimicrobials are not as effective as they once were.

Over time, many microbes have developed ways to circumvent the anti-microbial actions of the known antimicrobials, and in recent years there has been a worldwide increase in infections caused by microbes resistant to multiple antimicrobial agents. With the increased availability and ease of global travel, rapid spread of drug-resistant microbes around the world is becoming a serious problem. In the community, microbial resistance can result from nosocomial acquisition of drug-resistant pathogens (e.g., methicillin resistant *Staphylococcus aureus* (MRSA), vancomycin resistant *Enterococci* (VRE)), emergence of resistance due to use of antibiotics within the community (e.g., penicillin- and quinolone-resistant *Neisseria gonorrheae*), acquisition of resistant pathogens as a result of travel (e.g., antibiotic-resistant *Shigella*), or as a result of using antimicrobial agents in animals with subsequent transmission of resistant pathogens to humans (e.g., antibiotic resistant *Salmonella*). Antibiotic resistance in hospitals has usually resulted from overuse of antibiotics and has been a serious problem with MRSA, VRE, and multi-drug resistant Gram-negative bacilli (MDR-GNB) (e.g., *Enterobacter, Klebsiella, Serratia, Citrobacter, Pseudomonas*, and *E. coli*). In particular, catheter-related blood stream infections by bacteria and skin and soft tissue infections (SSTIs) are becoming an increasing problem.

Bacteria, viruses, fungi, and parasites have all developed resistance to known antimicrobials. Resistance usually results from three mechanisms: (i) alteration of the drug target such that the antimicrobial agent binds poorly and thereby has a diminished effect in controlling infection; (ii) reduced access of the drug to its target as a result of impaired drug penetration or active efflux of the drug; and (iii) enzymatic inactivation of the drug by enzymes produced by the microbe. Antimicrobial resistance provides a survival advantage to microbes and makes it harder to eliminate microbial infections from the body. This increased difficulty in fighting microbial infections has led to an increased risk of developing infections in hospitals and other settings. Diseases such as tuberculosis, malaria, gonorrhea, and childhood ear infections are now more difficult to treat than they were just a few decades ago. Drug resistance is a significant problem for hospitals harboring critically ill patients who are less able to fight off infections without the help of antibiotics. Unfortunately, heavy use of antibiotics in these patients selects for changes in microbes that bring about drug resistance. These drug resistant bacteria are resistant to our strongest antibiotics and continue to prey on vulnerable hospital patients. It has been reported that 5 to 10 percent of patients admitted to hospitals acquire an infection during their stay and that this risk has risen steadily in recent decades.

In view of these problems, there is an increasing need for novel antimicrobials to combat microbial infections and the problem of increasing drug resistance. A renewed focus on antimicrobial drug discovery is critical as pathogens are developing resistance to available drugs.

Synthetic compounds have thus far failed to replace natural antibiotics and to lead to novel classes of broad-spectrum compounds, despite the combined efforts of combinatorial synthesis, high-throughput screening, advanced medicinal chemistry, genomics and proteomics, and rational drug design. The problem with obtaining new synthetic antibiotics may be related in part to the fact that the synthetic antibiotics are invariably pumped out across the outer membrane barrier of bacteria by Multidrug Resistance pumps (MDRs). The outer membrane of bacteria is a barrier for amphipathic compounds (which essentially all drugs are), and MDRs extrude drugs across this barrier. Evolution has produced antibiotics that can largely bypass this dual barrier/extrusion mechanism, but synthetic compounds almost invariably fail.

SUMMARY OF THE INVENTION

Accordingly, the present invention provides novel antimicrobial compounds that are capable of combating microbial infections to overcome the problem of increasing drug resistance. In some embodiments, the present invention provides an isolated compound of Formula (I):

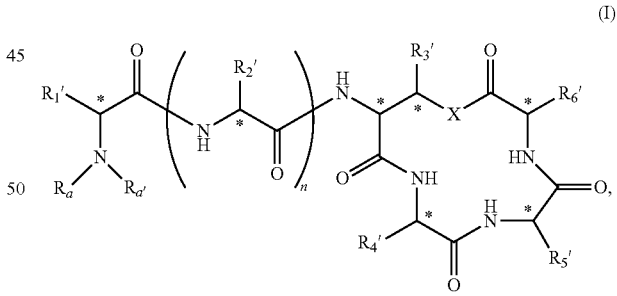

or an enantiomer, diastereomer, tautomer, or pharmaceutically acceptable salt thereof, wherein:
  each stereocenter is indicated with an "*" and may be, independently, either R or S configuration;
  each $R_1'$, $R_2'$, $R_3'$, $R_4'$, $R_5'$ and $R_6'$ is independently selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, $-NR_bR_b'$, $-COR_c$, $-COOR_d$, $-CONR_eR_e'$ and an amino acid side chain;

wherein each $R_a$, $R_a'$, $R_b$, $R_b'$, $R_c$, $R_d$, $R_e'$ and $R_{e'}$ is independently selected from the group consisting of hydrogen, substituted or unsubstituted alkyl, substituted or unsubstituted cycloalkyl, substituted or unsubstituted cycloalkenyl and substituted or unsubstituted aryl;

X is —O—, —S— or —N—; and n is an integer from 1 to 5. In some embodiments, n is an integer from 2 to 4.

In one specific embodiment, X is —O—. In another specific embodiment, X is —N—. In yet another specific embodiment, X is —S—.

unsubstituted alkyl. In a specific aspect, the substituted or unsubstituted alkyl is isobutyl.

In some embodiments, $R_3$ is substituted or unsubstituted alkyl, e.g., butyl substituted with an amino group. In some embodiments, $R_4$ is substituted or unsubstituted alkyl, e.g., methyl substituted with a hydroxyl group. In some aspects, $R_5$ is —$CONR_eR_e'$. In further aspects, $R_e$ and $R_e'$ are both hydrogen. In some embodiments, $R_6$ is substituted or unsubstituted alkyl, e.g., methyl. In some aspects, $R_7$ is substituted or unsubstituted alkyl, e.g., isobutyl. In some aspects, $R_8$ is substituted or unsubstituted alkyl, e.g., isobutyl.

In some embodiments, the isolated compound is of Formula (III):

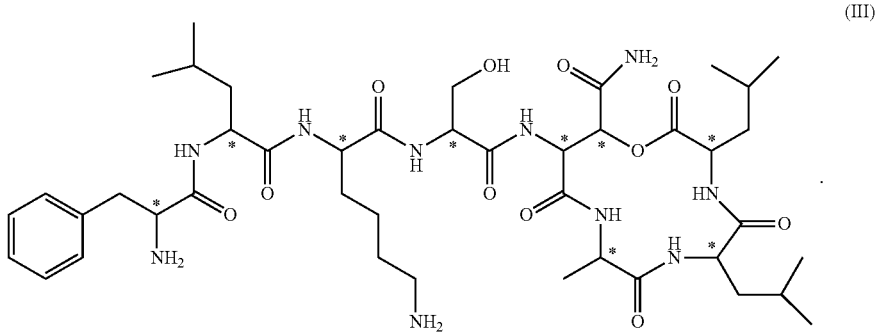 [SMILES: CC(C)CC(NC(=O)C(N)Cc1ccccc1)C(=O)NC(CCCCN)C(=O)NC(CO)C(=O)NC1C(=O)NC(C)C(=O)NC(CC(C)C)C(=O)NC(CC(C)C)C(=O)OC1C(N)=O]

(III)

In some aspects, the isolated compound is of Formula (II):

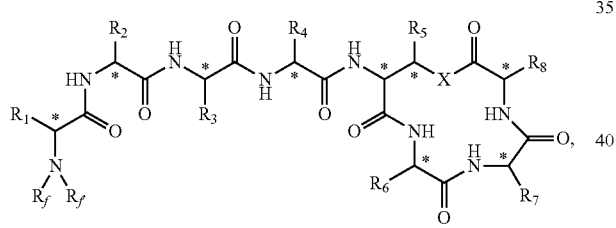

(II)

or an enantiomer, diastereomer, tautomer, or pharmaceutically acceptable salt thereof, wherein:
each stereocenter is indicated with an "*" and may be, independently, either R or S configuration;
each $R_1$, $R_2$, $R_3$, $R_4$, $R_5$, R6, $R_7$ and $R_8$ is independently selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, —$NR_bR_b'$, —$COR_c$, —$COOR_d$, —$CONR_eR_e'$ and an amino acid side chain;
wherein each $R_b$, $R_b'$, $R_c$, $R_d$, $R_e$, $R_e'$, $R_f$ and $R_f'$ is independently selected from the group consisting of hydrogen, substituted or unsubstituted alkyl, substituted or unsubstituted cycloalkyl, substituted or unsubstituted cycloalkenyl and substituted or unsubstituted aryl; and X is —O—, —S— or —N—.

In one specific embodiment, X is —O—. In another specific embodiment, X is —N—. In yet another specific embodiment, X is —S—.

In some aspects, $R_1$ is benzyl. In some aspects, $R_a$ and $R_a'$ are both hydrogen. In some aspects, $R_2$ is substituted or In some embodiments, the isolated compound of the invention is selected from the group consisting of the following compounds:

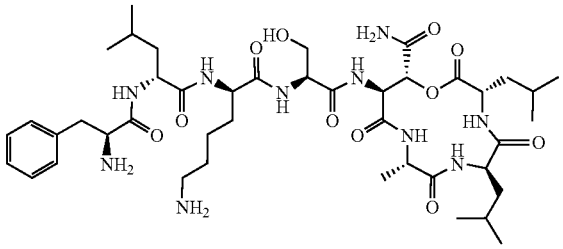

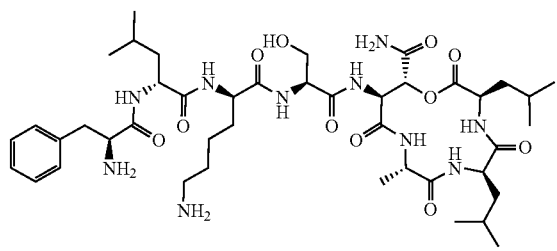

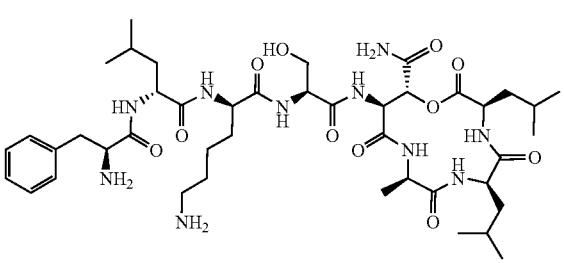

-continued

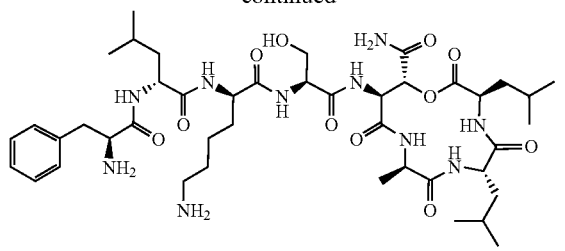

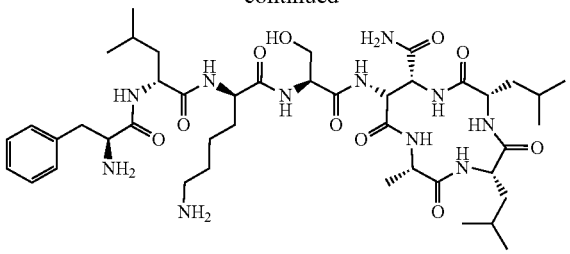

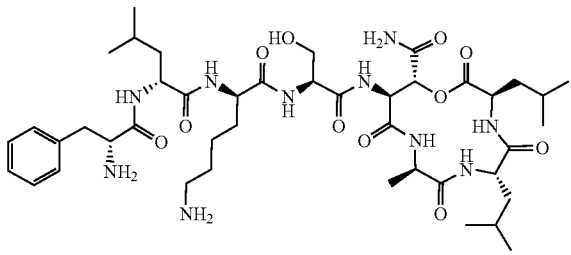

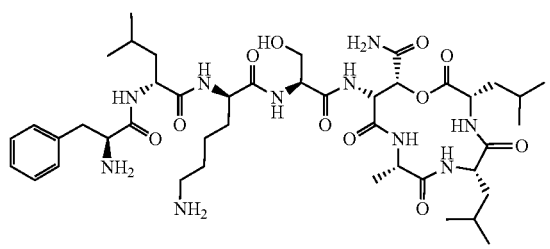

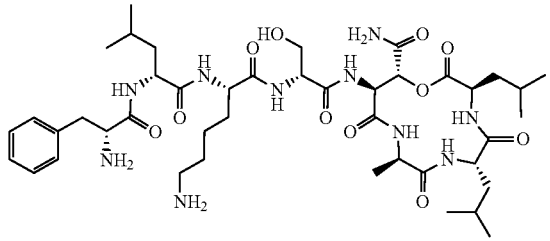

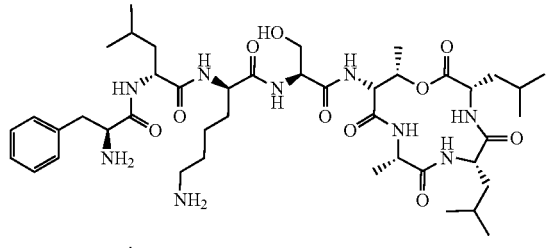

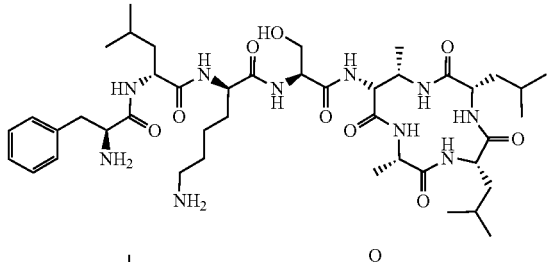

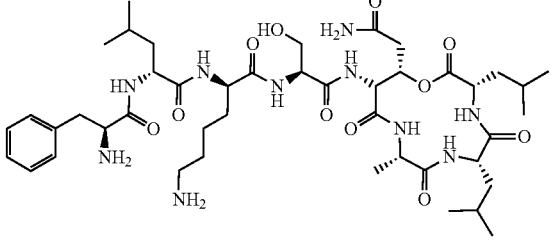

In some aspects, the present invention provides a culture medium comprising a compound of the invention as described above. In further aspects, the culture medium also comprises a bacterial cell belonging to the class of Beta-Proteobacteria.

In some embodiments, the present invention also provides a bacterial lysate comprising a compound of the invention as described above. In further aspects, the bacterial lysate is produced from a bacterial cell belonging to the class of Beta-Proteobacteria. In some aspects, the bacterial cell is a cultured bacterial cell.

In some embodiments, the present invention also provides a pharmaceutical composition comprising a compound of the invention as described above and a pharmaceutically acceptable excipient, carrier or diluent. In some embodiments, the pharmaceutical composition further comprises an agent selected from the group consisting of an antibiotic, an antifungal agent, an antiviral agent, an anti-protozoan agent, an anthelminthic agent, an anti-neoplastic agent, an immunoregulating agent, an anti-hypercholesterolemia agent and combinations thereof.

In some embodiments, the present invention also comprises a method of producing a compound of the invention as described above, comprising cultivating a bacterial cell belonging to the class of Beta-Proteobacteria in a culture medium, wherein the culture medium comprises an assimilable source of carbon, nitrogen and inorganic salts under aerobic conditions, thereby producing the compound. In further embodiments, the method also comprises isolating the compound.

In some embodiments, the present invention also provides a compound prepared according to the method as described above, e.g., compound of Formula (I).

In some aspects, the present invention also provides a method of treating a disorder in a subject in need thereof that comprises administering to the subject an effective amount of a compound of the invention as described above, thereby treating the disorder in the subject.

In some embodiments, the subject is selected from the group consisting of an animal and a plant. In further aspects, the animal is a mammal, e.g., a human or a domestic animal.

In some aspects, the disorder is caused by a pathogen selected from the group consisting of a bacterium, a fungus, a virus, a protozoan, a helminth, a parasite and combinations thereof.

In one aspect, the pathogen is a bacterium. In a further aspect, the bacterium is a Gram-positive bacterium, e.g., a Gram-positive bacterium belonging to the genus selected from the group consisting of *Streptococcus, Staphylococcus, Enterococcus, Corynebacteria, Listeria, Bacillus, Erysipelothrix, Mycobacterium, Clostridium*, and *Actinomycetales*. In some aspects, the Gram-positive bacterium belongs to the genus or species selected from the group consisting of methicillin-susceptible and methicillin-resistant staphylococci (including *Staphylococcus aureus, Staphylococcus* epidermidis, Staphylococcus haemolyticus, Staphylococcus hominis, Staphylococcus saprophyticus, and coagulase-negative staphylococci), glycopeptide intermediate-susceptible Staphylococcus aureus (GISA), penicillin-susceptible and penicillin-resistant streptococci (including Streptococcus pneumoniae, Streptococcus pyogenes, Streptococcus agalactiae, Streptococcus dysgalactiae, Streptococcus avium, Streptococcus bovis, Streptococcus lactis, Streptococcus sangius, Streptococcus anginosus, Streptococcus intermedius, Streptococcus constellatus and Streptococci Group C, Streptococci Group G and Viridans streptococci), enterococci (including vancomycin-susceptible and vancomycin-resistant strains such as Enterococcus faecalis and Enterococcus faecium), Clostridium difficile, Clostridium clostridiiforme, Clostridium innocuum, Clostridium perfringens, Clostridium tetani, Mycobacterium tuberculosis, Mycobacterium avium, Mycobacterium intracellulare, Mycobacterium kansaii, Mycobacterium gordonae, Mycobacteria sporozoites, Listeria monocytogenes, Bacillus subtilis, Bacillus anthracis, Corynebacterium diphtherias, Corynebacterium jeikeium, Corynebacterium sporozoites, Erysipelothrix rhusiopathiae, Staphylococcus warneri and Actinomyces israelli.

In one specific embodiment, the bacterium is Bacillus anthracis.

In some embodiments, the bacterium is a Gram-negative bacterium, e.g., a Gram-negative bacterium belonging to a genus or species selected from the group consisting of Helicobacter pylori, Legionella pneumophilia, Neisseria gonorrhoeae, Neisseria meningitidis, pathogenic Campylobacter sporozoites, Haemophilus influenzae, Pseudomonas aeruginosa, Enterobacter aerogenes, Enterobacter cloacae, Klebsiella pneumoniae, Klebsiella oxytoca, Pasteurella multocida, Bacteroides sporozoites, Bacteriodes fragilis, Bacteriodes thetaiotaomicron, Bacteriodes uniformis, Bacteriodes vulgatus Fusobacterium nucleatum, Streptobacillus moniliformis, Leptospira, Escherichia coli, Salmonella enterica, Salmonella salamae, Salmonella arizonae, Salmonella diarizonae, Salmonella houtenae, Salmonella bongori, Salmonella indica, Salmonella Enteritidis, Salmonella typhi, and Citrobacter freundii.

In some aspects, the pathogen a virus, e.g., a virus selected from the group consisting of Retroviridae, Picornaviridae, Calciviridae, Togaviridae, Flaviridae, Coronaviridae, Rhabdoviridae, Filoviridae, Paramyxoviridae, Orthomyxoviridae, Bungaviridae, Arenaviridae, Reoviridae, Birnaviridae, Hepadnaviridae, Parvoviridae, Papovaviridae, Adenoviridae, Herpesviridae, Poxviridae, and Iridoviridae. In a further embodiment, the virus is selected from the group consisting of influenza virus, human immunodeficiency virus, and herpes simplex virus.

In some aspects, the pathogen is a protozoan, e.g., a protozoan selected from the group consisting of Trichomonas vaginalis, Giardia lamblia, Entamoeba histolytica, Balantidium coli, Cryptosporidium parvum and Isospora belli, Trypansoma cruzi, Trypanosoma gambiense, Leishmania donovani, and Naegleria fowleri.

In some embodiments, the pathogen is a helminth, e.g., a helminth selected from the group consisting of Schistosoma mansoni, Schistosoma cercariae, Schistosoma japonicum, Schistosoma mekongi, Schistosoma hematobium, Ascaris lumbricoides, Strongyloides stercoralis, Echinococcus granulosus, Echinococcus multilocularis, Angiostrongylus cantonensis, Angiostrongylus constaricensis, Fasciolopis buski, Capillaria philippinensis, Paragonimus westermani, Ancylostoma dudodenale, Necator americanus, Trichinella spiralis, Wuchereria bancrofti, Brugia malayi, and Brugia timori, Toxocara canis, Toxocara cati, Toxocara vitulorum, Caenorhabiditis elegans, and Anisakis species.

In some aspects, the pathogen is a parasite, e.g., a parasite selected from the group consisting of Plasmodium falciparum, Plasmodium yoelli, Hymenolepis nana, Clonorchis sinensis, Loa boa, Paragonimus westermani, Fasciola hepatica, and Toxoplasma gondii. In further aspects, the parasite is a malarial parasite.

In some embodiments, the pathogen is a fungus, e.g., a fungus selected from the group consisting of Cryptococcus neoformans, Histoplasma capsulatum, Coccidioides immitis, Blastomyces dermatitidis, Chlamydia trachomatis, Candida albicans, Candida tropicalis, Candida glabrata, Candida krusei, Candida parapsilosis, Candida dubliniensis, Candida lusitaniae, Epidermophyton floccosum, Microsporum audouinii, Microsporum canis, Microsporum canis var. distortum Microsporum cookei, Microsporum equinum, Microsporum ferrugineum, Microsporum fulvum, Microsporum gallinae, Microsporum gypseum, Microsporum nanum, Microsporum persicolor, Trichophyton ajelloi, Trichophyton concentricum, Trichophyton equinum, Trichophyton flavescens, Trichophyton gloriae, Trichophyton megnini, Trichophyton mentagrophytes var. erinacei, Trichophyton mentagrophytes var. interdigitale, Trichophyton phaseoliforme, Trichophyton rubrum, Trichophyton rubrum downy strain, Trichophyton rubrum granular strain, Trichophyton schoenleinii, Trichophyton simii, Trichophyton soudanense, Trichophyton terrestre, Trichophyton tonsurans, Trichophyton vanbreuseghemii, Trichophyton verrucosum, Trichophyton violaceum, Trichophyton yaoundei, Aspergillus fumigatus, Aspergillus flavus, and Aspergillus clavatus.

In some aspects, the present invention also provides a method of inhibiting growth of an infectious agent that comprises contacting the agent with a compound of the invention as described above. In some aspects, the infectious agent is cultured in vitro.

In some embodiments, the present invention also provides a method of inhibiting peptidoglycan synthesis in a bacterial cell that comprises contacting the bacterial cell with a compound of the invention as described above.

BRIEF DESCRIPTION OF THE DRAWINGS

FIG. 1 is a bar graph illustrating the average number of bacterial colonies (expressed as average log 10 CFU/gram of thigh) in a neutropenic mouse thigh infection model infected with S. aureus ATCC 33591 and treated with a compound of the invention and vancomycin.

DETAILED DESCRIPTION OF THE INVENTION

The present invention generally relates to novel depsipeptides, to processes for the preparation of these novel depsipeptides, to pharmaceutical compositions comprising the novel depsipeptides, and to methods of using the novel depsipeptides to treat or inhibit various disorders, e.g., bacterial infections. The present invention relates to a novel antibiotic that has broad activity against many bacterial pathogens, including strains resistant to other antibiotics, and in particular, Gram-positive pathogens. The compounds disclosed herein have favorable bioavailability and low toxicity.

Definitions

For convenience, certain terms employed in the specification, examples, and appended claims are collected here.

Unless defined otherwise, all technical and scientific terms used herein have the same meaning as commonly understood by one of ordinary skill in the art to which this invention belongs. The initial definition provided for a group or term herein applies to that group or term throughout the present specification individually or as part of another group, unless otherwise indicated.

The articles "a" and "an" are used herein to refer to one or to more than one (i.e., to at least one) of the grammatical object of the article. By way of example, "an element" means one element or more than one element.

The term "or" is used herein to mean, and is used interchangeably with, the term "and/or," unless context clearly indicates otherwise.

The term "substantially the same" is used herein to mean that two subjects being compared share at least 90% of a common feature. In certain embodiments, the two subjects share at least 95% of a common feature. In certain other embodiments, the two subjects share at least 99% of a common feature.

The term "isolated" is used herein to refer to compounds of the invention being substantially free from other materials associated with it in its natural environment. For example an isolated compound can be substantially free of contaminating materials, such as cellular material, contaminating materials from the cell from which the compound is derived, chemical precursors or other chemicals when chemically synthesized. Substantially free of other materials refers generally to, for example, less than about 30%, or 20%, or 15%, or 10%, or 5%, or 2% (by dry weight) impurities. In some embodiments, the isolated compounds are substantially pure. In some embodiments, the preparation of a compound having less than about 10% (by dry weight) of contaminating materials from the cell, or of chemical precursors is considered to be substantially pure. In other embodiments, the preparation of a compound having less than about 5%, about 4%, about 3%, about 2%, about 1% (by dry weight) of contaminating materials from the cell, or of chemical precursors is considered to be substantially pure.

Unless otherwise indicated, any heteroatom with unsatisfied valences is assumed to have hydrogen atoms sufficient to satisfy the valences.

The term "heating" includes, but not limited to, warming by conventional heating (e.g., electric heating, steam heating, gas heating, etc.) as well as microwave heating.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to a patient.

The term "treating" with regard to a subject, refers to improving at least one symptom of the subject's disorder. Treating can be curing the disorder or condition, or improving it.

The term "disorder" is used herein to mean, and is used interchangeably with, the terms disease, condition, or illness, unless the context clearly indicates otherwise.

The term "microbe" is used herein to mean an organism such as a bacterium, a virus, a protozoan, or a fungus, especially one that transmits disease.

The phrase "pharmaceutically acceptable" is employed herein to refer to those compounds, materials, compositions, and/or dosage forms which are, within the scope of sound medical judgment, suitable for use in contact with the tissues of human beings, animals and plants without excessive toxicity, irritation, allergic response, or other problem or complication, commensurate with a reasonable benefit/risk ratio.

Throughout the specification, groups and substituents thereof may be chosen to provide stable moieties and compounds.

Compounds of the Invention

In some embodiments, the present teachings relate to an isolated compound of Formula

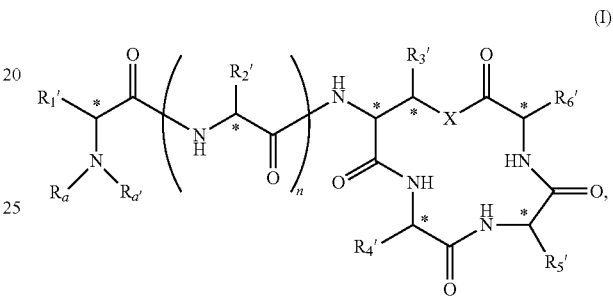

(I)

or an enantiomer, diastereomer, tautomer, or pharmaceutically acceptable salt thereof, wherein:

each stereocenter is indicated with an "*" and may be, independently, either R or S configuration;

each $R_1'$, $R_2'$, $R_3'$, $R_4'$, $R_5'$ and $R_6'$ is independently selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, $-NR_bR_b'$, $-COR_c$, $-COOR_d$, $-CONR_eR_e'$ and an amino acid side chain;

wherein each $R_a$, $R_a'$, $R_b$, $R_b'$, $R_c$, $R_d$, $R_e$ and $R_e'$ is independently selected from the group consisting of hydrogen, substituted or unsubstituted alkyl, substituted or unsubstituted cycloalkyl, substituted or unsubstituted cycloalkenyl and substituted or unsubstituted aryl;

X is $-O-$, $-S-$ or $-N-$; and n is an integer from 1 to 5.

In one specific embodiment, X is $-O-$. In another specific embodiment, X is $-N-$. In yet another specific embodiment, X is $-S-$.

In one embodiment, n is an integer from 1 to 2. In one embodiment, n is an integer from 2 to 3. In another embodiment, n is an integer from 3 to 4. In yet another embodiment, n is an integer from 4 to 5. In some embodiments, n is 1, 2, 3, 4 or 5.

In some embodiments, the amino acid side chain is a natural amino acid side chain. In other embodiments, the amino acid side chain is an unnatural amino acid side chain.

In some embodiments, $R_a$ and $R_a'$ are both hydrogen.

In some embodiments, $R_b$ and $R_b'$ are both hydrogen.

In some embodiments, $R_e$ and $R_e'$ are both hydrogen.

In some embodiments, the present teachings relate to an isolated compound of Formula (II):

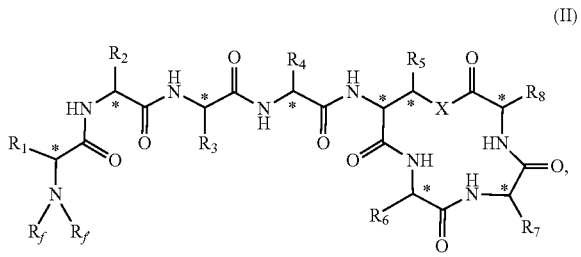

or an enantiomer, diastereomer, tautomer, or pharmaceutically acceptable salt thereof, wherein:
  each stereocenter is indicated with an "*" and may be, independently, either R or S configuration;
  each $R_1$, $R_2$, $R_3$, $R_4$, $R_5$, $R_6$, $R_7$ and $R_8$ is independently selected from the group consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted aryl, —$NR_bR_b'$, —$COR_c$, —$COOR_d$, —$CONR_eR_e'$ and an amino acid side chain;
    wherein each $R_b$, $R_b'$, $R_c$, $R_d$, $R_e$, $R_e'$, $R_f$ and $R_f'$ is independently selected from the group consisting of hydrogen, substituted or unsubstituted alkyl, substituted or unsubstituted cycloalkyl, substituted or unsubstituted cycloalkenyl and substituted or unsubstituted aryl; and
  X is —O—, —S— or —N—.

In one specific embodiment, X is —O—. In another specific embodiment, X is —N—. In yet another specific embodiment, X is —S—.

In some examples, X is —O— and $R_f$ and $R_f'$ are both hydrogen.

In some examples, $R_1$ may be benzyl. In some examples, $R_2$ may be a substituted or unsubstituted alkyl, e.g., methyl, ethyl, propyl, isopropyl, butyl or isobutyl. In one specific embodiment, $R_2$ is isobutyl.

In some examples, $R_3$ may be a substituted or unsubstituted alkyl, e.g., butyl substituted with an amino group. In some examples, $R_4$ may be a substituted or unsubstituted alkyl, e.g., methyl substituted with a hydroxyl group. In some examples, $R_5$ may be a substituted or unsubstituted alkyl, e.g., methyl, ethyl, propyl, isopropyl, butyl or isobutyl, or —$CONR_eR_e'$. In one aspect, $R_5$ is methyl. In another aspect, $R_5$ is —$CONR_eR_e'$, and both $R_e$ and $R_e'$, are hydrogen.

In some aspects, $R_6$ may be a substituted or unsubstituted alkyl, e.g., methyl, ethyl, propyl, isopropyl, butyl or isobutyl. In one specific embodiment, $R_2$ is methyl. In some examples, $R_7$ may be a substituted or unsubstituted alkyl, e.g., methyl, ethyl, propyl, isopropyl, butyl or isobutyl. In one specific embodiment, $R_7$ is isobutyl. In some examples, $R_8$ may be a substituted or unsubstituted alkyl, e.g., methyl, ethyl, propyl, isopropyl, butyl or isobutyl. In one specific embodiment, $R_8$ is isobutyl.

In some embodiments, each $R_1$, $R_2$, $R_3$, $R_4$, $R_5$, $R_6$, $R_7$ and $R_8$ may be, independently, an amino acid side chain, e.g., a D-amino acid side chain or an L-amino acid side chain. The amino acid side chain may be a natural amino acid chain, e.g., a side chain of alanine, arginine, asparagine, aspartic acid, cysteine, glutamine, glutamic acid, glycine, histidine, isoleucine, leucine, lysine, methionine, phynylananine, proline, serine, threonine, tryptophan, tyrosine or valine. The amino acid side chain may also be an unnatural amino acid side chain, e.g., a side chain of any unnatural amino acid known in the art. Non-limiting examples of unnatural amino acid side chains include side chains of unnatural amino acids as listed, e.g., in a Sigma-Aldrich Catalog, the entire contents of which are incorporated herein by reference. In one embodiment, the unnatural amino acid side chain may be β-hydroxyglutamine.

For example, in some embodiments, $R_1$ may be a side chain of phenylalanine, e.g., D-phenylalanine or L-phenylalanine. In some examples, $R_2$, $R_7$ or $R_8$ may be a side chain of leucine, e.g., D-leucine or L-leucine. In some examples, $R_3$ may be a side chain of lysine, e.g., D-lysine or L-lysine. In some examples, $R_4$ may be a side chain of serine, e.g., D-serine or L-serine. In some examples, $R_6$ may be a side chain of alanine, e.g., D-alanine or L-alanine.

In some embodiments, $R_b$ and $R_b'$ are both hydrogen. In some embodiments, $R_e$ and $R_e'$ are both hydrogen. In some embodiments, $R_f$ and $R_f'$ are both hydrogen.

The terms "alkyl" refers to a straight or branched chain aliphatic group containing from 1 to 12 carbon atoms, e.g., from 1 to 6 carbon atoms for straight chain or from 3 to 6 carbon atoms for branched chain). Exemplary "alkyl" groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like.

The term "alkenyl" refers to a straight or branched chain hydrocarbon group containing from 2 to 12 carbon atoms, e.g., from 2 to 6 carbon atoms for straight chain, or from 3 to 6 carbon atoms for branched chain, and at least one carbon-carbon double bond. Exemplary "alkenyl" groups include ethenyl, propenyl, butenyl, pentenyl, hexenyl, heptenyl, octenyl, nonenyl, decenyl, and the like.

The term "alkynyl" refers to a straight or branched chain hydrocarbon group containing from 2 to 12 carbon atoms, e.g., from 2 to 6 carbon atoms for straight chain or from 3 to 6 carbon atoms for branched chain, and at least one carbon to carbon triple bond. Exemplary such groups include ethylenyl, propenyl, butenyl, pentenyl, hexenyl, heptenyl, octenyl, nonenyl, decenyl, and the like.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, cycloheptyl, cyclooctyl and the like. The term "cykloalkyl" further includes cycloalkyl groups which may further include oxygen, nitrogen, sulfur or phosphorous atoms replacing one or more carbons of the hydrocarbon backbone.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc.

The term "aryl" refers to cyclic, aromatic hydrocarbon groups containing 1 to 5 aromatic rings, especially monocyclic or bicyclic groups such as phenyl, biphenyl or naphthyl. Where containing two or more aromatic rings (e.g., bicyclic or tricyclic), the aromatic rings of the aryl group may be joined at a single point (e.g., biphenyl), or fused (e.g., naphthyl, phenanthrenyl and the like). The term "aryl" also refers to groups, e.g., 5- and 6-membered single-ring aromatic groups, that may include from zero to four heteroatoms, such as pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics".

Alkyl, alkenyl, alkynyl, cycloalkyl, cycloalkenyl or aryl groups as described in the present teachings may be unsubstituted or substituted. The term "substituted" refers to alkyl, alkenyl, alkynyl, cycloalkyl, cycloalkenyl or aryl groups having at least one, e.g., one, two, three, four or more, substituent replacing a hydrogen on one or more carbons of the hydrocarbon backbone. Such substituents may include, for example, alkyl, alkenyl, alkynyl, acetyl, aryl, hydroxyl, halogen (e.g., —Br, —Cl, —I or —F), —OR, SR, $NR_2$, COOH, COOR or COR, wherein R is a hydrogen or an alkyl containing from 1 to 6 carbons.

In some examples, the isolated compound of the invention is a compound of Formula (III):

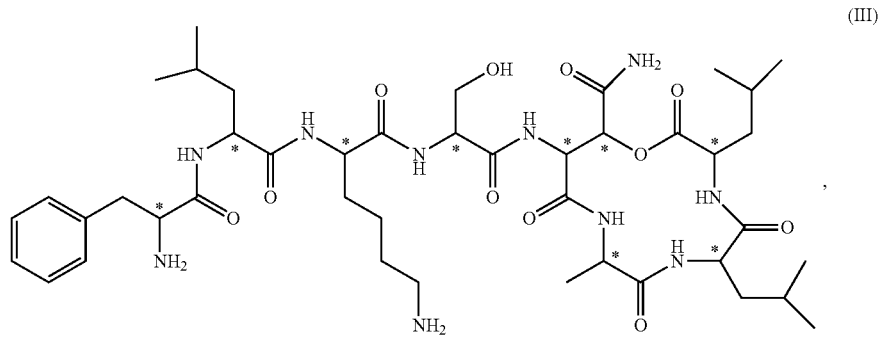 [SMILES: CC(C)CC(NC(=O)C(N)Cc1ccccc1)C(=O)NC(CCCCN)C(=O)NC(CO)C(=O)NC1C(=O)NC(C)C(=O)NC(CC(C)C)C(=O)NC(CC(C)C)C(=O)OC1C(N)=O]

(III)

wherein each stereocenter is indicated with an "*" and may be, independently, either R or S configuration.

In some embodiments, the isolated compound is a compound having a structure as shown in Table 1 below.

TABLE 1

Compounds of the Invention

| No. | Structure |
|---|---|
| 1 | 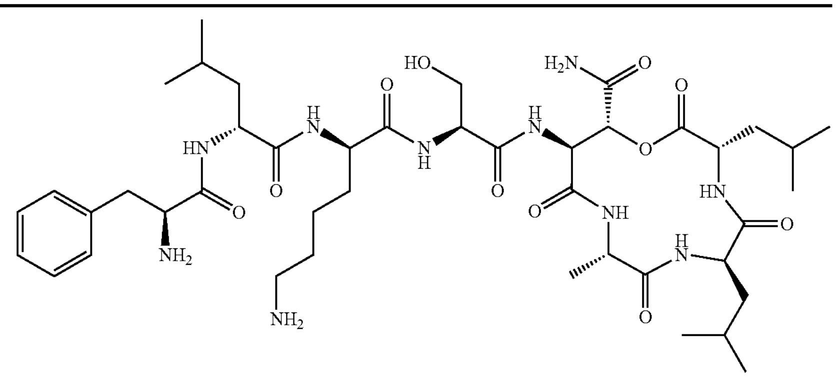 |
| 2 | 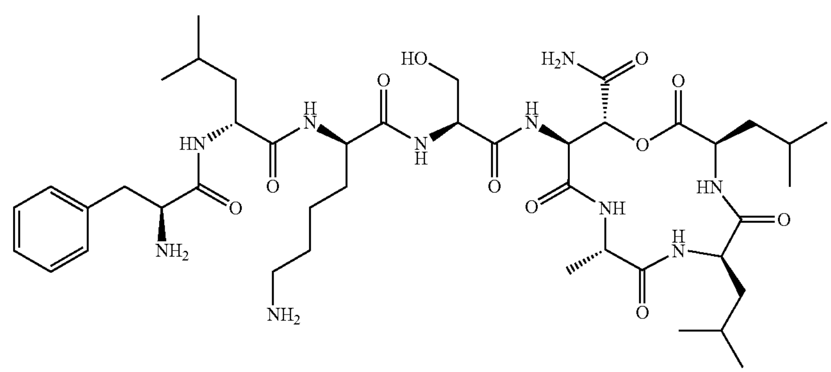 [SMILES: CC(C)C[C@H]1NC(=O)[C@H](C)NC(=O)[C@@H](NC(=O)[C@H](CO)NC(=O)[C@@H](CCCCN)NC(=O)[C@@H](CC(C)C)NC(=O)[C@@H](N)Cc2ccccc2)[C@H](C(N)=O)OC(=O)[C@@H](CC(C)C)NC1=O] |

TABLE 1-continued

Compounds of the Invention

| No. | Structure |
|---|---|
| 3 | 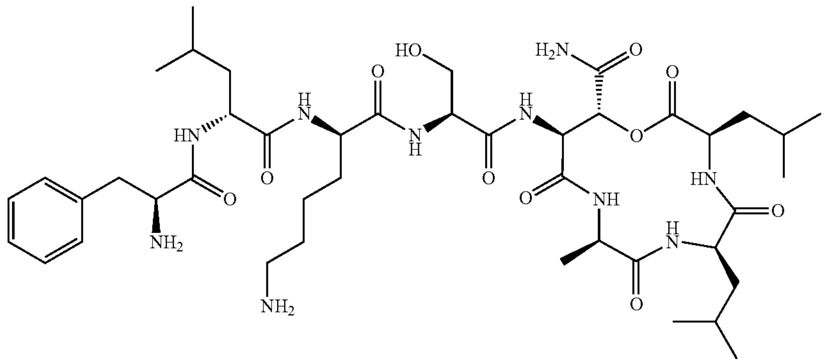 [SMILES: CC(C)C[C@@H](NC(=O)[C@@H](N)Cc1ccccc1)C(=O)N[C@H](CCCCN)C(=O)N[C@@H](CO)C(=O)N[C@@H]1C(=O)N[C@H](C)C(=O)N[C@H](CC(C)C)C(=O)N[C@H](CC(C)C)C(=O)O[C@H]1C(N)=O] |
| 4 | 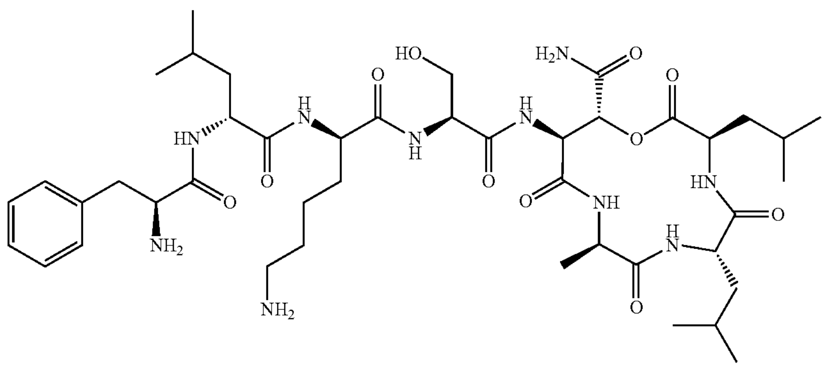 [SMILES: CC(C)C[C@@H]1NC(=O)[C@@H](C)NC(=O)[C@@H](NC(=O)[C@H](CO)NC(=O)[C@@H](CCCCN)NC(=O)[C@@H](CC(C)C)NC(=O)[C@@H](N)Cc2ccccc2)[C@H](C(N)=O)OC(=O)[C@@H](CC(C)C)NC1=O] |
| 5 | 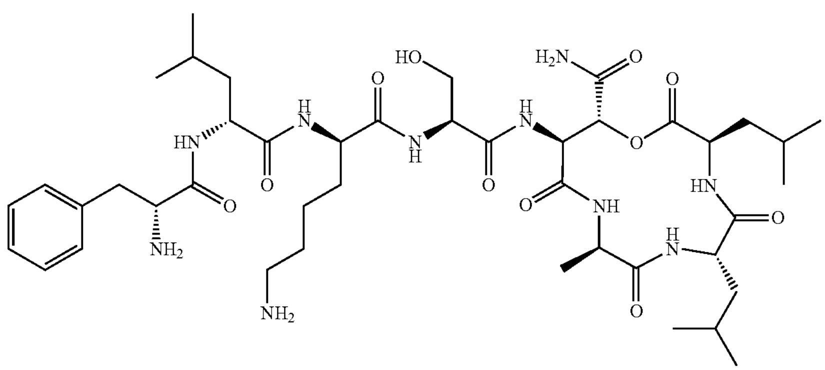 [SMILES: CC(C)C[C@@H]1NC(=O)[C@@H](C)NC(=O)[C@@H](NC(=O)[C@H](CO)NC(=O)[C@@H](CCCCN)NC(=O)[C@@H](CC(C)C)NC(=O)[C@H](N)Cc2ccccc2)[C@H](C(N)=O)OC(=O)[C@@H](CC(C)C)NC1=O] |
| 6 | 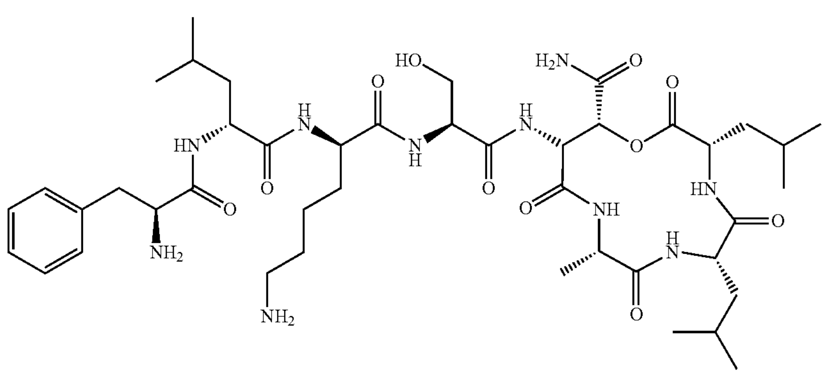 |

US 11,891,415 B2
TABLE 1-continued
Compounds of the Invention
| No. | Structure |
|---|---|
| 7 | 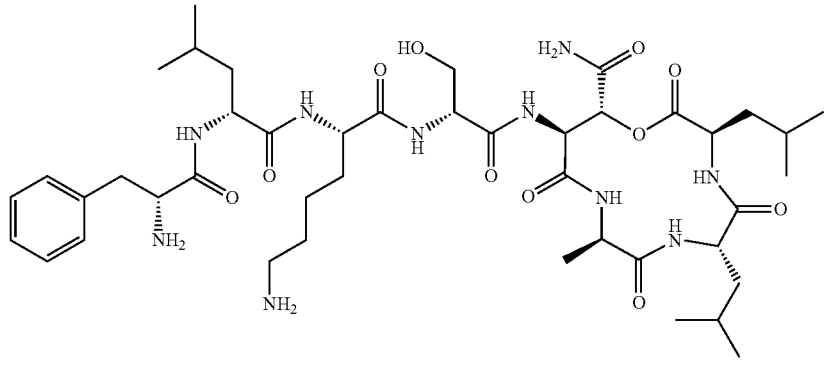 [SMILES: CC(C)C[C@@H]1NC(=O)[C@@H](C)NC(=O)[C@@H](NC(=O)[C@@H](CO)NC(=O)[C@H](CCCCN)NC(=O)[C@@H](CC(C)C)NC(=O)[C@H](N)Cc2ccccc2)[C@H](C(N)=O)OC(=O)[C@@H](CC(C)C)NC1=O] |
| 8 | 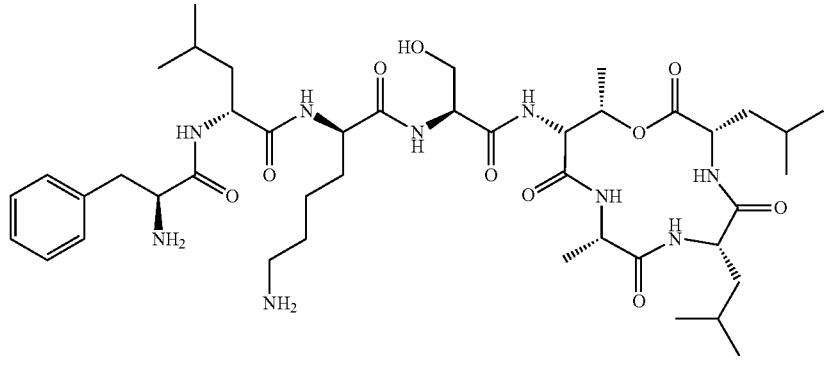 |
| 9 | 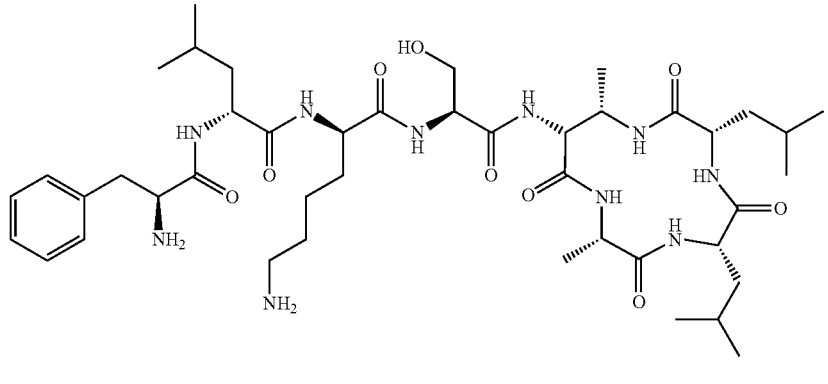 |
| 10 | 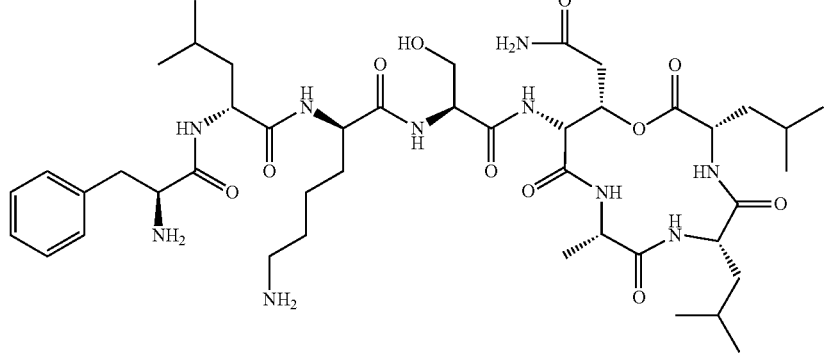 |

TABLE 1-continued

Compounds of the Invention

| No. | Structure |
|---|---|
| 11 | *(chemical structure)* |

In some embodiments, a compound of the invention, e.g., a compound of Formula (III), may be referred to as Novo29. Novo29 is a depsipeptide having molecular weight of 902 g/mole. Without wishing to be bound by theory, it is believed that Novo29 may be a peptidoglycan synthesis inhibitor that may exert its actibacterial properties by acting through binding lipid II and lipid III.

In some embodiments, compounds of the invention do not show gelate when added to serum at up to 500 μg/mL.

In some embodiments, any carbon or hydrogen in the compounds of the invention, e.g., compounds of Formula (I), (II), (III), or compounds of Table 1, may also be replaced with $^{13}C$ or $^{2}H$, respectively.

The phrase "compound of the invention", "a compound of Formula (I)", "a compound of Formula (II)", "a compound of Formula (III)", or "a compound of Table 1", as used herein, is meant to include enantiomers, diastereomers, tautomers, and pharmaceutically-acceptable salts thereof. Depsipeptide compounds of the present invention, and salts thereof, may exist in their tautomeric form (for example, as an amide or guanidine). All such tautomeric forms are contemplated herein as part of the present invention. A compound of the invention, e.g., a compound isolated from a beta-proteobacterium, may also be referred to as "Novo29". In some embodiments, the present teachings relate to a mixture of stereoisomers. In other embodiments, the present teachings specifically relate to a single stereoisomer of a compound of the invention.

In some embodiments, the compound of the invention is an isolated natural product of a bacterial species. For example, in some embodiments, the compound of the invention is an isolated natural product of a previously uncultivated beta-proteobacterium.

All stereoisomers of the depsipeptide compounds of the present invention (for example, those which may exist due to asymmetric carbons on various substituents), including enantiomeric forms and diastereomeric forms, are contemplated within the scope of this present invention. In one embodiment, compounds of the invention are mixtures. Alternatively, however, compounds of the invention are single stereoisomers substantially free of other stereoisomers (e.g., as a pure or substantially pure optical isomer having a specified activity). In some embodiments, the present invention relates to a single stereoisomer in the presence of less than about 10% (by dry weight) other isomers. In some embodiments, the present invention relates to a single stereoisomer in the presence of less than about 5% (by dry weight) other isomers. In some embodiments, the present invention relates to a single stereoisomer in the presence of less than about 2% (by dry weight) other isomers. In some embodiments, the present invention relates to a single stereoisomer in the presence of less than about 1% (by dry weight) other isomers. In some embodiments, the present invention relates to a single stereoisomer in the presence of about 5% (by dry weight) to about 10% (by dry weight) other isomers. In some embodiments, the present invention relates to a single stereoisomer in the presence of about 1% (by dry weight) to about 5% (by dry weight) other isomers. In some embodiments, the present invention relates to a single stereoisomer in the presence of about 1% (by dry weight) to about 10% (by dry weight) other isomers. In some embodiments, the present invention relates to a single stereoisomer in the presence of about 5% (by dry weight) to about 10% (by dry weight) other isomers. Non-related compounds make up less than 2% (by dry weight). In other embodiments, the present teachings are directed to mixtures of stereoisomers. The chiral centers of the compounds of the invention may have the S or R configuration as defined by the IUPAC 1974 Recommendations. The stereoisomeric forms can be resolved by physical methods, such as, for example, fractional crystallization, separation or crystallization of diastereomeric derivatives or separation by chiral column chromatography. The individual optical isomers can be obtained from a mixture of stereoisomers by any suitable method, including without limitation, conventional methods, such as, for example, salt formation with an optically active acid followed by crystallization.

Depsipeptide compounds of the present invention may be, subsequent to their preparation, e.g., isolated and purified to obtain a composition containing an amount by weight equal to or greater than 90% (by dry weight), which is then used or formulated as described herein. Depsipeptide compounds of the present invention may be, subsequent to their preparation, e.g., isolated and purified to obtain a composition containing an amount by weight equal to or greater than 95% (by dry weight), which is then used or formulated as described herein. Depsipeptide compounds of the present invention may be, subsequent to their preparation, e.g., isolated and purified to obtain a composition containing an amount by weight of about 90% (by dry weight) to about 95% (by dry weight), which is then used or formulated as described herein. Depsipeptide compounds of the present invention may be, subsequent to their preparation, e.g., isolated and purified to obtain a composition containing an amount by weight of about 85% (by dry weight) to about 95% (by dry weight), which is then used or formulated as described herein. Depsipeptide compounds of the present invention may be, subsequent to their preparation, e.g., isolated and purified to obtain a composition containing an amount by weight of about 95% (by dry weight) to about 99% (by dry weight), which is then used or formulated as described herein.

All configurational isomers of the compounds of the present invention are contemplated, either in admixture or in pure or substantially pure form.

In another embodiment, the present invention relates to a pharmaceutical composition comprising a compound described in the present teachings and a pharmaceutically-acceptable excipient, carrier, or diluent. In certain embodiments, the composition further includes an agent selected from the group consisting of an antibiotic, an antifungal agent, an antiviral agent, an anti-protozoan agent, an anthelminthic agent, an anti-neoplastic agent, an immunoregulating agent, an anti-hypercholesterolemia agent and combinations thereof.

The depsipeptide compounds of the present invention may form salts which are also within the scope of this present invention. Reference to a compound of the present invention herein is understood to include reference to salts thereof, unless otherwise indicated. The term "salt(s)", as employed herein, denotes acidic salts formed with inorganic and/or organic acids. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound of the invention with an amount of acid, such as an equivalent amount, in a medium such as one in which the salt precipitates or in an aqueous or aqueous and organic medium followed by lyophilization.

The depsipeptide compounds of the present invention which contain a basic moiety, such as, but not limited to an amine, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemi sulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

Methods of Preparing the Compounds of the Invention

The present teachings also relate to methods for producing a compound of the invention, e.g., a compound of Formula (I), Formula (II), Formula (III) or a compound of Table 1, as described above.

The method includes cultivating or culturing a beta-proteobacterium in a culture medium comprising assimilable sources of carbon, nitrogen, and inorganic salts under aerobic conditions, and enabling the production of an assayable amount of the compound of the invention.

In certain embodiments, the method further comprises isolating and/or purifying the compound of the invention. The compound of the invention may be isolated by centrifuging the fermentation broth (e.g., centrifuging at 10,000 rpm for 20 minutes) and isolating and/or purifying the compound of the invention, e.g., by reversed-phase chromatography.

In some embodiments, the method further comprises isolating and/or purifying the compound of the invention to at least about 75% purity (by dry weight), e.g., to at least about 80% purity (by dry weight), at least about 85% purity (by dry weight), at least about 90% purity (by dry weight), at least about 95% purity (by dry weight), at least about 97% purity (by dry weight), or at least about 99% purity (by dry weight).

In yet another embodiment, the present invention relates to a compound of the invention prepared according to the method described herein.

In some embodiments, the present invention also provides a culture medium comprising the compound of the invention, e.g., the compound of Formula (I), Formula (II), Formula (III) or the compound of Table 1. The culture medium may be a culture medium appropriate for culturing a bacterial cell, e.g., a bacterial cell belonging to the class of Beta-Proteobacteria.

In some embodiments, the present invention also provides a cell lysate, e.g., a bacterial cell lysate, comprising the compound of the invention, e.g., the compound of Formula (I), Formula (II), Formula (III) or the compound of Table 1. The bacterial cell lysate may be prepared using bacterial cells, e.g., cultured bacterial cells, belonging to the class of Beta-Proteobacteria.

Alternatively, compounds of the invention, e.g., compounds of Formula (I), Formula (II), Formula (III) or compounds of Table 1, may be synthesized by using synthesis methods known in the art.

Methods of Treatment Using the Compounds of the Invention

The present invention also provides methods of inhibiting the growth of a pathogen. The methods involve contacting the pathogen with an effective amount of one or more depsipeptide compounds of the invention, thereby inhibiting the growth of the pathogen compared with the growth of the pathogen in the absence of treatment with the compound. In certain embodiments, the method reduces the growth of the pathogen compared with the growth of the pathogen in the absence of treatment with the compound. In other instances, the treatment results in the killing of the pathogen. Non-limiting examples of a pathogen include, but are not limited to, a bacterium, a fungus, a virus, a protozoan, a helminth, a parasite, and combinations thereof. These methods may be practiced in vivo or in vitro.

The anti-bacterial activity of the depsipeptide compounds of the invention with respect to a specific bacterium can be assessed by in vitro assays such as monitoring the zone of inhibition and the minimal inhibitory concentration (MIC) assays. The anti-fungal activity of the depsipeptide compounds of the invention can be determined, for example, by following the viability of the desired fungal pathogens (such as *Candida albicans*, and *Aspergillus* species) for example as described in Sanati et al., A new triazole, voriconazole (UK-109,496), blocks sterol biosynthesis in *Candida albicans* and *Candida krusei*, Antimicrob. Agents Chemother., 1997 November; 41(11): 2492-2496, the entire contents of which are incorporated herein by reference. Anti-viral properties of the depsipeptide compounds of the invention can be determined, for example, by monitoring the inhibition of influenza neuraminidase or by assaying viral viability as described in Tisdale M., Monitoring of viral susceptibility: new challenges with the development of influenza NA inhibitors, *Rev. Med. Virol.*, 2000 January-February; 10(1): 45-55, the entire contents of which are incorporated herein by reference. Anti-protozoan activity of the depsipeptide compounds of the invention can be determined by following the viability of protozoan parasites such as *Trichomonas vaginalis* and *Giardia lamblia* as described in Katiyar et al., Antiprotozoal activities of benzimidazoles and correlations with beta-tubulin sequence, *Antimicrob. Agents Chemother.*, 1994 September; 38(9): 2086-2090, the entire contents of which are incorporated herein by reference. Anthelminthic activity of the depsipeptide compounds of the invention can be determined, for example, by following the effect of the compounds on the viability of nematodes such as *Schistosoma mansoni*, *Schistosoma cercariae* and *Caenorhabditis elegans* as described in Mølgaard P. et al., Traditional herbal remedies used for the treatment of urinary schistosomiasis in Zimbabwe, *J. Ethnopharmacol.*, 1994 April; 42(2):125-32, the entire contents of which are incorporated herein by reference.

In other embodiments, the present invention is directed to methods of treating a disorder, e.g., a pathogen infection, in a subject in need thereof, by administering to the subject an effective amount of one or more depsipeptide compounds described herein. In certain embodiments, the disorder is caused by a pathogen such as, but not limited to, a bacterium, a fungus, a virus, a protozoan, a helminth, a parasite, or a combination thereof.

In some embodiments, the disorder is caused by a bacterium. The depsipeptide compounds described herein can be useful against both Gram-positive and Gram-negative bacteria. In particular, the disorder may be caused by a Gram-positive bacterium. Alternatively, the disorder may be caused by a Gram-negative bacterium. Non-limiting examples of Gram-positive bacteria include bacteria belonging to the genus selected from the group consisting of *Streptococcus, Staphylococcus, Enterococcus, Corynebacteria, Listeria, Bacillus, Erysipelothrix,* and *Actinomycetes*. In some embodiments, the compounds of the invention are used to treat an infection by one or more of: *Helicobacter pylori, Legionella pneumophilia, Mycobacterium tuberculosis, Mycobacterium avium, Mycobacterium intracellulare, Mycobacterium kansaii, Mycobacterium gordonae, Mycobacteria sporozoites, Staphylococcus aureus, Staphylococcus epidermidis, Neisseria gonorrhoeae, Neisseria meningitidis, Listeria monocytogenes, Streptococcus pyogenes* (Group A Streptococcus), *Streptococcus agalactiae pyogenes* (Group B Streptococcus), *Streptococcus dysgalactia, Streptococcus faecalis, Streptococcus bovis, Streptococcus pneumoniae,* pathogenic *Campylobacter* sporozoites, *Enterococcus* sporozoites, *Haemophilus influenzae, Pseudomonas aeruginosa, Bacillus anthracis, Bacillus subtilis, Escherichia coli, Corynebacterium diphtherias, Corynebacterium jeikeium, Corynebacterium* sporozoites, *Erysipelothrix rhusiopathiae, Clostridium perfringens, Clostridium tetani, Clostridium difficile, Enterobacter aerogenes, Klebsiella pneumoniae, Pasturella multocida, Bacteroides thetaiotamicron, Bacteroides uniformis, Bacteroides vulgatus, Fusobacterium nucleatum, Streptobacillus moniliformis, Leptospira,* and *Actinomyces israelli.* In specific embodiments, the compounds described herein may be useful in treating an infection by Methicillin Resistant *Staphylococcus aureus* (MRSA) or by Vancomycin Resistant Entercocci (VRE). MRSA contributes to approximately 19,000 deaths annually in the United States. Although most of these deaths are due to hospital-acquired MRSA (HA-MRSA), community-acquired MRSA (CA-MRSA) is actually more virulent, and known to be potentially fatal to previously healthy individuals. The virulence of CA-MRSA is in part due to the expression of phenol soluble modulins or PSM peptides. Accordingly, in treating CA-MRSA, one can use a compound of the invention in combination with an agent that modulates the expression and/or activity of virulence factors, such as, but not limited to, PSM peptides. In certain embodiments, the depsipeptide compounds of the invention may be used to treat spirochetes such as *Borelia burgdorferi, Treponema pallidium,* and *Treponema pertenue.*

In a particular embodiment, the Gram-positive bacteria may be selected from *Staphylococcus* (including, for example, *S. aureus* spp., *S. epidermidis* spp., *S. warneri* spp. and *S. haemolyticus* spp.); *Streptococcus* (including, for example, *S. viridans* spp., *S. pneumoniae* spp., *S. agalactiae* spp., and *S. pyogenes* spp.); *Bacillus* (including, for example, *B. anthracis* spp. and *B. subtilis,* spp.); *Clostridium* (including, for example, *C. difficile* spp.); *Propionibacterium* (including, for example, *P. acnes* spp.); *Enterococcus* (including, for example, *E. faecium* spp., *E. faecalis* spp., Vancomycin-resistant *E. faecium* spp., and Vancomycin-resistant *E. faecalis* spp.); and *Mycobacterium* (including, for example, *M. smegmatis* spp. and *M. tuberculosis* spp.). The compounds described herein are useful for treating disorders caused by these bacteria. Examples of such disorders include acute bacterial skin and skin structure infections, *C. difficile* associated diarrhea, anthrax, sepsis, botulism, urinary tract infections, bacteremia, bacterial endocarditis, diverticulitis, meningitis, pneumonia, and tuberculosis.

In a particular embodiment, the Gram-negative bacteria are selected from *Haemophilus* (including for example, *H. influenzae* spp.); *Klebsiella* (including, for example, *K. pneumoniae* spp.); *Pseudomonas* (including, for example, *P. aeruginosa* spp.); *Escherichia* (including, for example, *E. coli* spp.); *Yersinia* (including, for example, *Y. pestis* spp.); *Neisseria* (including, for example, *N. gonorrhoeae* spp.); *Bacteriodes* (including, for example, *B. fragilis* spp.); *Proteus* (including, for example, *P. mirabilis* spp. and *P. vulgaris* spp.); *Enterobacter* (including, for example, *E. cloacae* spp. and *E. aerogenes* spp.; *Serratia* (including, for example, *S. marcescens* spp.); *Acinetobacter* (including, for example, *A. baumannii* spp.); and *Moraxella* (including, for example, *M. catarrhalis* spp.). In a specific embodiment, the Gram-negative bacteria is *Haemophilus*, and in particular, *H. influenzae;* or *Moraxella,* and in particular, *M. catarrhalis* spp. The compounds described herein are useful for treating disorders caused by these bacteria. Examples of such disorders include influenza, bacteremia, pneumonia, acute bacterial meningitis, gonorrhea, urinary tract infections, respiratory tract infections, catheter-associated bacteremia, wound infections, otitis media, bronchitis, sinusitis, and laryngitis.

In other embodiments, the depsipeptide compounds described herein may be useful in treating viral disorders. Non-limiting examples of infectious viruses that may cause the disorders to be treated by the compounds of the invention include: *Retroviridae* (e.g., human immunodeficiency viruses, such as HIV-1 (also referred to as HTLV-III, LAV or HTLV-III/LAV), or HIV-III; and other isolates, such as HIV-LP; *Picornaviridae* (e.g., polio viruses, hepatitis A virus; enteroviruses, human coxsackie viruses, rhinoviruses, echoviruses); *Calciviridae* (e.g., strains that cause gastroenteritis); *Togaviridae* (e.g., equine encephalitis viruses, rubella viruses); *Flaviridae* (e.g., dengue viruses, encephalitis viruses, yellow fever viruses); *Coronaviridae* (e.g., coronaviruses, severe acute respiratory syndrome (SARS) virus); *Rhabdoviridae* (e.g., vesicular stomatitis viruses, rabies viruses); *Filoviridae* (e.g., ebola viruses); *Paramyxoviridae* (e.g., parainfluenza viruses, mumps virus, measles virus, respiratory syncytial virus); *Orthomyxoviridae* (e.g., influenza viruses); *Bungaviridae* (e.g., Hantaan viruses, bunga viruses, phleboviruses and Nairo viruses); *Arenaviridae* (hemorrhagic fever viruses); *Reoviridae* (e.g., reoviruses, orbiviurses and rotaviruses); *Birnaviridae*; *Hepadnaviridae* (e.g, Hepatitis B virus); *Parvoviridae* (parvoviruses); *Papovaviridae* (papilloma viruses, polyoma viruses); *Adenoviridae* (most adenoviruses); *Herpesviridae* (e.g., herpes simplex virus (HSV) 1 and 2, varicella zoster virus, cytomegalovirus (CMV), herpes viruses); *Poxviridae* (e.g., variola viruses, vaccinia viruses, pox viruses); and *Iridoviridae* (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parentally transmitted, i.e., Hepatitis C); Norwalk and related viruses, and astroviruses). In specific embodiments, the compounds of the invention are used to treat an influenza virus, human immunodeficiency virus, and herpes simplex virus.

In some embodiments, the depsipeptide compounds of the invention may be useful for treating disorders caused by fungi. Non-limiting examples of fungi that may be inhibited by the compounds of the invention include, but are not limited to, *Cryptococcus neoformans, Histoplasma capsulatum, Coccidioides immitis, Blastomyces dermatitidis, Chlamydia trachomatis, Candida albicans, Candida tropicalis, Candida glabrata, Candida krusei, Candida parapsilosis, Candida dubliniensis, Candida lusitaniae, Epidermophyton floccosum, Microsporum audouinii, Microsporum canis, Microsporum canis* var. *distortum Microsporum cookei, Microsporum equinum, Microsporum ferrugineum, Microsporum fulvum, Microsporum gallinae, Microsporum gypseum, Microsporum nanum, Microsporum persicolor, Trichophyton ajelloi, Trichophyton concentricum, Trichophyton equinum, Trichophyton flavescens, Trichophyton gloriae, Trichophyton megnini, Trichophyton mentagrophytes* var. *erinacei, Trichophyton mentagrophytes* var. *interdigitale, Trichophyton phaseoliforme, Trichophyton rubrum, Trichophyton rubrum downy strain, Trichophyton rubrum granular strain, Trichophyton schoenleinii, Trichophyton simii, Trichophyton soudanense, Trichophyton terrestre, Trichophyton tonsurans, Trichophyton vanbreuseghemii, Trichophyton verrucosum, Trichophyton violaceum, Trichophyton yaoundei, Aspergillus fumigatus, Aspergillus flavus,* and *Aspergillus clavatus.*

In yet other embodiments, the depsipeptide compounds described herein may be useful in treating disorders caused by protozoans. Non-limiting examples of protozoa that may be be inhibited by the compounds of the invention include, but are not limited to, *Trichomonas vaginalis, Giardia lamblia, Entamoeba histolytica, Balantidium coli, Cryptosporidium parvum* and *Isospora belli, Trypansoma cruzi, Trypanosoma gambiense, Leishmania donovani*, and *Naegleria fowleri.*

In certain embodiments, the depsipeptide compounds described herein are useful in treating disorders caused by helminths. Non-limiting examples of helminths that may be inhibited by the compounds of the invention include, but are not limited to: *Schistosoma mansoni, Schistosoma cercariae, Schistosoma japonicum, Schistosoma mekongi, Schistosoma hematobium, Ascaris lumbricoides, Strongyloides stercoralis, Echinococcus granulosus, Echinococcus multilocularis, Angiostrongylus cantonensis, Angiostrongylus constaricensis, Fasciolopis buski, Capillaria philippinensis, Paragonimus westermani, Ancylostoma dudodenale, Necator americanus, Trichinella spiralis, Wuchereria bancrofti, Brugia malayi,* and *Brugia timori, Toxocara canis, Toxocara cati, Toxocara vitulorum, Caenorhabiditis elegans,* and *Anisakis* species.

In some embodiments, the depsipeptide compounds described herein are useful in treating disorders caused by parasites. Non-limiting examples of parasites that may be inhibited by the compounds of the invention include, but are not limited to, *Plasmodium falciparum, Plasmodium yoelli, Hymenolepis nana, Clonorchis sinensis, Loa boa, Paragonimus westermani, Fasciola hepatica,* and *Toxoplasma gondii.* In specific embodiments, the parasite is a malarial parasite.

In other embodiments, the depsipeptide compounds may be used to inhibit the growth of an infective agent compared with the growth of the infective agent in the absence of being treated by the compound. Non-limiting examples of infective agents include, but are not limited to, bacteria, fungi, viruses, protozoa, helminthes, parasites, and combinations thereof. The depsipeptide compounds may be used to inhibit the agent in vivo or in vitro.

Pharmaceutical Compositions Comprising the Compounds of the Invention

The present invention also provides pharmaceutical compositions comprising at least one of the depsipeptide compounds of the invention, and a pharmaceutically-acceptable carrier, such as a carrier that solubilizes the depsipeptide compounds of the invention. These depsipeptide compositions are suitable for administration to a subject (e.g., a mammal such as a human). The pharmaceutical composition may be used for treating a disorder. Non-limiting examples of such disorders are provided above and include an infection by a pathogen, e.g., a bacterium.

In one embodiment, the depsipeptide compounds are administered in a pharmaceutically-acceptable carrier. Any suitable carrier known in the art may be used. Carriers that efficiently solubilize the compounds of the invention are preferred. Carriers include, but are not limited to, a solid, liquid, or a mixture of a solid and a liquid. The carriers may take the form of capsules, tablets, pills, powders, lozenges, suspensions, emulsions, or syrups. The carriers may include substances that act as flavoring agents, lubricants, solubilizers, suspending agents, binders, stabilizers, tablet disintegrating agents, and encapsulating materials. The phrase "pharmaceutically-acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Non-limiting examples of materials which may serve as pharmaceutically-acceptable carriers include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline, (18) Ringer's solution, (19) ethyl alcohol; (20) phosphate buffer solutions; and (21) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single-dosage form will vary depending upon the subject being treated, the particular mode of administration, and the particular condition being treated, among others. The amount of active ingredient that can be combined with a carrier material to produce a single-dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the invention with the carrier and, optionally, one or more accessory ingredients. In general, the formulations are prepared by uniformly and intimately bringing into association a depsipeptide compound of the invention with liquid carriers, or timely divided solid carriers, or both, and then, if necessary, shaping the product.

In solid dosage forms for oral administration (e.g., capsules, tablets, pills, dragees, powders, granules, and the like), the active ingredient is mixed with one or more additional ingredients, such as sodium citrate or dicalcium phosphate, and/or any of the following: fillers or extenders, such as, but not limited to, starches, lactose, sucrose, glucose, mannitol, and/or silicic acid; binders, such as, but not limited to, carboxymethylcellulose, alginates, gelatin, polyvinyl pyrrolidone, sucrose, and/or acacia; humectants, such as, but not limited to, glycerol; disintegrating agents, such as, but not limited to, agar, calcium carbonate, potato or tapioca starch, alginic acid, certain silicates, and sodium carbonate; solution retarding agents, such as, but not limited to, paraffin; absorption accelerators, such as, but not limited to, quaternary ammonium compounds; wetting agents, such as, but not limited to, cetyl alcohol and glycerol monostearate; absorbents, such as, but not limited to, kaolin and bentonite clay; lubricants, such as, but not limited to, talc, calcium stearate, magnesium stearate, solid polyethylene glycols, sodium lauryl sulfate, and mixtures thereof; and coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

In powders, the carrier is a finely-divided solid, which is mixed with an effective amount of a finely-divided agent. Powders and sprays can contain, in addition to a compound of the invention, excipients, such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Tablets for systemic oral administration may include one or more excipients as known in the art, such as, for example, calcium carbonate, sodium carbonate, sugars (e.g., lactose, sucrose, mannitol, sorbitol), celluloses (e.g., methyl cellulose, sodium carboxymethyl cellulose), gums (e.g., arabic, tragacanth), together with one or more disintegrating agents (e.g., maize, starch, or alginic acid, binding agents, such as, for example, gelatin, collagen, or acacia), lubricating agents (e.g., magnesium stearate, stearic acid, or talc), inert diluents, preservatives, disintegrants (e.g., sodium starch glycolate), surface-active and/or dispersing agent. A tablet may be made by compression or molding, optionally with one or more accessory ingredients.

In solutions, suspensions, emulsions or syrups, an effective amount of the depsipeptide compound is dissolved or suspended in a carrier, such as sterile water or an organic solvent, such as aqueous propylene glycol. Other compositions can be made by dispersing the compound in an aqueous starch or sodium carboxymethyl cellulose solution or a suitable oil known to the art. The liquid dosage forms may contain inert diluents commonly used in the art, such as, for example, water or other solvents, solubilizing agents and emulsifiers, such as, but not limited to, ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, and fatty acid esters of sorbitan, and mixtures thereof.

Besides inert diluents, the oral compositions can also include adjuvants, such as wetting agents, emulsifying and suspending agents, sweetening, flavoring, coloring, perfuming, and preservative agents.

Suspensions, in addition to the active compound, may contain suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of the pharmaceutical compositions for rectal or vaginal administration may be presented as a suppository, which may be prepared by mixing one or more compounds of the invention with one or more suitable non-irritating excipients or carriers comprising, for example, cocoa butter, polyethylene glycol, a suppository wax or a salicylate, and which is solid at room temperature but liquid at body temperature and, thus, will melt in the rectum or vaginal cavity and release the agents. Formulations suitable for vaginal administration also include pessaries, tampons, creams, gels, pastes, foams, or spray formulations containing such carriers as are known in the art to be appropriate.

Dosage forms for the topical or transdermal administration of a compound of the invention include powders, sprays, ointments, pastes, creams, lotions, gels, solutions, drops, patches, and inhalants. The active depsipeptide compound may be mixed under sterile conditions with a pharmaceutically-acceptable carrier, and with any preservatives, buffers, or propellants that may be required.

Ointments, pastes, creams, and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound of the invention to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the depsipeptide compound in a polymer matrix or gel.

The depsipeptide compounds are administered in an effective amount to a subject in need of such treatment. The phrase "effective amount" as used herein means the amount of a compound of the invention, or composition comprising the compound of the invention, that is effective for producing some desired effect in an animal. It is recognized that when an agent is being used to achieve a therapeutic effect, the actual dose which comprises the "effective amount" will vary depending on a number of conditions including, but not limited to, the particular condition being treated, the severity of the disease, the size and health of the patient, the route of administration. A skilled medical practitioner can readily determine the appropriate dose using methods well known in the medical arts. In some embodiments, an effective amount is an amount effective in treating a disorder in a subject in need thereof. Furthermore, a skilled practitioner will appreciate that the effective amount of the depsipeptide compound may be lowered or increased by fine-tuning and/or by administering more than one depsipeptide compound, or by administering a depsipeptide compound together with a second agent (e.g., antibiotics, antifungals, antivirals, NSAIDS, DMARDS, steroids, etc.). An effective amount may be determined, for example, empirically by starting at relatively low amounts and by step-wise increments with concurrent evaluation of beneficial effect (e.g., reduction in symptoms). The actual effective amount will be established by dose/response assays using methods standard in the art (Johnson et al., *Diabetes*. 42:1179, (1993)). As is known to those in the art, the effective amount will depend on bioavailability, bioactivity, and biodegradability of the depsipeptide compound.

In some embodiments, an effective amount is an amount that is capable of reducing the symptoms of the disorder in a subject. Accordingly, the amount can vary with the subject being treated. For example, the effective amount of the depsipeptide compound may comprise from about 1 µg/kg body weight to about 100 mg/kg body weight. In one embodiment, the effective amount of the compound comprises from about 1 µg/kg body weight to about 50 mg/kg body weight. In a further embodiment, the effective amount of the compound comprises from about 10 µg/kg body weight to about 10 mg/kg body weight. When one or more depsipeptide compounds or agents are combined with a carrier, they may be present in an amount of about 1 weight percent to about 99 weight percent, the remainder being composed of the pharmaceutically-acceptable carrier. In some embodiments, an effective amount is between about 1 mg and about 10 g per dose, e.g., between about 10 mg and about 1 g per dose. Values and ranges intermediate to the above-recited ranges are intended to be encompassed by the present teachings.

Administration of the depsipeptide compound may be hourly, daily, weekly, monthly, yearly, or a single event. In addition, administration can have a duration of from one day to one year or more. In some embodiments, administration refers to daily administration for a period of time, e.g., for about a week, two weeks, three weeks, one month, three months, six months or a year. In some embodiments, administration refers to weekly administration for a period of time, e.g., for about a month, three months, six months, one year or more.

The present invention also provides for kits that comprise at least one depsipeptide compound of the invention. The kits may contain at least one container and may also include instructions directing the use of these materials. In another embodiment, a kit may include an agent used to treat the disorder in question with or without such above-mentioned materials that may be present to determine if a subject has an inflammatory disease.

Administration of the Pharmaceutical Compositions of the Invention

Methods of administration of the formulations of the present invention comprising the depsipeptide compounds of the invention described herein can be by any of a number of methods well known in the art. These methods include local or systemic administration. Exemplary routes of administration include oral, parenteral, transdermal, intradermal, intramuscular, intraperitoneal, intravenous, subcutaneous, intranasal (e.g., nebulizer, inhaler, aerosol dispenser), intraocular (e.g., for the treatment of conjunctivitis), intraaural (e.g., for the treatment of ear infections), colorectal, rectal, intravaginal, and any combinations thereof. In addition, it may be desirable to introduce the pharmaceutical compositions of the present invention into the central nervous system by any suitable route, including intraventricular and intrathecal injection. Intraventricular injection may be facilitated by an intraventricular catheter, for example, attached to a reservoir, such as an Ommaya reservoir. Methods of introduction may also be provided by rechargeable or biodegradable devices, e.g., depots. Furthermore, it is contemplated that administration may occur by coating a device, implant, stent, or prosthetic. The compounds of the invention can also be used to coat catheters in any situation where catheters are inserted in the body.

In another embodiment, the subject depsipeptide compounds can be administered as part of a combination therapy with other agents. Combination therapy refers to any form of administration combining two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either simultaneously or sequentially. Thus, an individual who receives such treatment can have a combined effect of different therapeutic compounds.

For example, depsipeptide compounds may be used in combination with other known antibiotics. The depsipeptide compounds of the invention may either be administered sequentially or substantially at the same time. Varying the antibiotic can be helpful in reducing the ability of the pathogen to develop resistance to the drug. Non-limiting examples of antibiotics include penicillins (e.g., natural penicillins, penicillinase-resistant penicillins, antipseudomonal penicillins, aminopenicillins), tetracyclines, macrolides (e.g., erythromycin), lincosamides (e.g., clindamycin), streptogramins (e.g., Synercid), aminoglycosides, and sulfonamides. In some embodiments, the depsipeptide compounds of the invention are used in combination with compounds that target virulence factors such as, but not limited to, phenol-soluble modulins. In some embodiments, the depsipeptide compounds of the invention are used in combination with compounds that target the efflux pumps of the pathogens.

Kits and Articles of Manufacture Comprising Pharmaceutical Compositions of Compounds of the Invention Also within the scope of the present invention are kits comprising the compounds of the invention, or a pharmaceutically acceptable salt thereof, and instructions for use. The term "kit" as used herein refers to a packaged product comprising components with which to administer a pharmaceutical composition comprising the compounds of the invention, or a pharmaceutically acceptable salt thereof, of the invention for treatment of a disorder caused by a pathogen. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles or bottles containing a dropper suitable for the dropwise administration of a solution containing the compounds of the invention, e.g., into the ear or eye of a subject. The kit can also include instructions for administering a pharmaceutical composition comprising compounds of the invention, or a pharmaceutically acceptable salt thereof. In a particular embodiment, the kit may comprise (a) a pharmaceutical composition comprising a compound of the invention or a pharmaceutically acceptable salt thereof, wherein the pharmaceutical composition is in a container; and (b) instructions describing a method of using the pharmaceutical composition.

The kit can further contain one more additional reagent, such as an antibiotic, an antifungal agent, an antiviral agent, an anti-protozoan agent, an anthelminthic agent, an anti-neoplastic agent, an immunoregulating agent, an anti-hypercholesterolemia agent and combinations thereof. Kits typically include a label indicating the intended use of the contents of the kit. The term label includes any writing, or recorded material supplied on or with the kit, or which otherwise accompanies the kit.

The invention also provides a pharmaceutical pack or kit comprising one or more containers filled with a liquid formulation of a pharmaceutical composition comprising a compound of the invention, or a pharmaceutically acceptable salt thereof. In one embodiment, a container filled with a liquid formulation of the invention is a pre-filled syringe. In a specific embodiment, the formulations of the invention are formulated in single dose vials as a sterile liquid. For example, the formulations may be supplied in 3 cc USP Type I borosilicate amber vials (West Pharmaceutical Services—Part No. 6800-0675) with a target volume of 1.2 mL. Optionally associated with such container(s) can be a notice in the form prescribed by a governmental agency regulating the manufacture, use or sale of pharmaceuticals or biological products, which notice reflects approval by the agency of manufacture, use or sale for human administration.

Any pre-filled syringe known to one of skill in the art may be used in combination with a liquid formulation of the invention. Pre-filled syringes that may be used are described in, for example, but not limited to, PCT Publications WO05032627, WO08094984, WO9945985, WO03077976, U.S. Pat. Nos. 6,792,743, 5,607,400, 5,893,842, 7,081,107, 7,041,087, 5,989,227, 6,807,797, 6,142,976, 5,899,889, US Patent Publications US20070161961A1, US20050075611A1, US20070092487A1, US20040267194A1, US20060129108A1. Pre-filled syringes may be made of various materials. In one embodiment a pre-filled syringe is a glass syringe. In another embodiment a pre-filled syringe is a plastic syringe. One of skill in the art understands that the nature and/or quality of the materials used for manufacturing the syringe may influence the stability of a compound formulation stored in the syringe. For example, it is understood that silicon based lubricants deposited on the inside surface of the syringe chamber may affect particle formation in the compound formulation. In one embodiment, a pre-filled syringe comprises a silicone based lubricant. In one embodiment, a pre-filled syringe comprises baked on silicone. In another embodiment, a pre-filled syringe is free from silicone based lubricants. One of skill in the art also understands that small amounts of contaminating elements leaching into the formulation from the syringe barrel, syringe tip cap, plunger or stopper may also influence stability of the formulation. For example, it is understood that tungsten introduced during the manufacturing process may adversely affect formulation stability. In one embodiment, a pre-filled syringe may comprise tungsten at a level above 500 ppb. In another embodiment, a pre-filled syringe is a low tungsten syringe. In another embodiment, a pre-filled syringe may comprise tungsten at a level between about 500 ppb and about 10 ppb, between about 400 ppb and about 10 ppb, between about 300 ppb and about 10 ppb, between about 200 ppb and about 10 ppb, between about 100 ppb and about 10 ppb, between about 50 ppb and about 10 ppb, between about 25 ppb and about 10 ppb.

The present invention also encompasses a finished packaged and labeled pharmaceutical product. This article of manufacture includes the appropriate unit dosage form in an appropriate vessel or container such as a glass vial, pre-filled syringe or other container that is hermetically sealed. In one embodiment, the unit dosage form is provided as a sterile particulate free solution comprising pharmaceutical composition comprising a compound of the invention, or a pharmaceutically acceptable salt thereof, that is suitable for parenteral administration. In another embodiment, the unit dosage form is provided as a sterile lyophilized powder comprising a pharmaceutical composition comprising a compound of the invention, or a pharmaceutically acceptable salt thereof, that is suitable for reconstitution.

In one embodiment, the unit dosage form is suitable for intravenous, intramuscular, intranasal, oral, topical or subcutaneous delivery. Thus, the invention encompasses sterile solutions suitable for each delivery route. The invention further encompasses sterile lyophilized powders that are suitable for reconstitution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question, as well as how and how frequently to administer the pharmaceutical. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, pre-filled syringe, sprayer, insufflator, intravenous (i.v.) bag, envelope and the like; and at least one unit dosage form of a compound of the invention contained within the packaging material, wherein the compound comprises a liquid formulation containing an antibiotic. The packaging material includes instruction means which indicate how that the compound can be used to prevent, treat and/or manage one or more symptoms associated with a disease or disorder.

The present invention is further illustrated by the following examples which should not be construed as limiting in any way. Throughout this application, various patents, patent applications, and publications are referenced. The disclosures of these patents, patent applications, and publications in their entireties are hereby incorporated by reference into this application. The instant disclosure will govern in the instance that there is any inconsistency between the patents, patent applications, and publications and this disclosure.

EXAMPLES

Example 1

Isolation and Chemical Structure of a Compound of the Invention

A compound of Formula (III) has been isolated from an extract produced by a previously uncultivated beta-proteobacterium. An isolate of the beta-proteobacteium was grown on an agar plate, and then one colony was used to inoculate broth. After fermentation, the broth was centrifuged, and the supernatant was adsorbed onto a reversed-phase resin. After washing, the compound of the invention was eluted from the resin and further purified using HPLC. Structure of the compound of the invention was determined using NMR and mass spectrometry.

Example 2

Antibacterial Activity of a Compound of the Invention

The spectrum of the antibacterial activity of the compound of Formula (III) was determined and is shown in Table 2.

TABLE 2

| Antibacterial test panel | |
|---|---|
| Strain | Minimum Inhibitory Concentration (MIC, μg/mL) |
| Staphylococcus aureus | |
| NCTC 8325-4 (MSSA) | 0.5-1 |
| ATCC 29213 (MSSA) | 0.5-1 |
| ATCC 700699 (GISA) | 1-2 |
| NRS71 (Epidemic MRSA) | 1 |
| NRS108 (MRSA, also synercid$^R$) | 1 |
| ATCC 33591 (MRSA) | 1-2 |
| Staphylococcus epidermidis | |
| ATCC 35982 (mecA positive) | 0.5 |
| NRS8 (mecA positive) | 0.5 |
| Staphylococcus haemolyticus | |
| NRS9 (mecA positive) | 1 |
| NRS69 (mecA positive) | 0.5 |
| Other Gram-positive | |
| VRE faecium BM4147 (aac(6')-le-aph-(2')) | 0.5-1 |
| VRE faecalis ATCC 51299 | 0.5-2 |
| B. subtilis 1A1 | 1-2 |
| B. anthracis Sterne | 0.25 |
| S. pyogenes ATCC19615 | 0.25-0.5 |

TABLE 2-continued

| Antibacterial test panel | |
|---|---|
| Strain | Minimum Inhibitory Concentration (MIC, μg/mL) |
| S. warneri NRS138 | 1 |
| M tuberculosis $MC^2$ 6020 | 0.5-1 |
| Gram-negative | |
| H. influenzae SJ7 | 2 |
| E. coli K12 | 64 |
| E. coli WO153 (AB1157:asmB1 ΔtolC::kan) | 1-2 |
| P. aeruginosa PA-01 | >128 |

The results in Table 2 demonstrate that the compound of Formula (III) has excellent activity against Gram-positive pathogens, including strains resistant to other peptidoglycan inhibitors, and lower activity against most Gram-negative bacteria. The presence of 10% serum had no effect on the minimum inhibitory MIC values. The compound of Formula (III) shows excellent bactericidal activity against S. aureus, with an minimum bactericidal concentration (MBC) of 2×MIC.

Example 3

Frequency of Resistance

The attempts to generate spontaneous resistant mutants of S. aureus were unsuccessful (tested up to $1.2 \times 10^{10}$ CFU). This indicates an excellent spontaneous resistance frequency of $<10^{-10}$ (tested at 4×MIC).

Example 4

Specificity of Action: Macromolecular Synthesis Studies

To gain insight into the mechanism and specificity of action of the compound of Formula (III), a macromolecular synthesis study with S. aureus was performed. Incorporation of tritiated thymidine, uridine, leucine, or N-acetyl-glucosamine into DNA, RNA, protein, or peptidoglycan showed that the compound of Formula (III) strongly inhibited peptidoglycan synthesis (comparable to vancomycin) and no other major pathway.

Example 5

Cytotoxicity and Hemolytic Activity

The compound of the invention displayed no cytotoxicity against two mammalian cell lines, NIH3T3 and HepG2 at 64 μg/mL (the highest dose tested). The compound of Formula (III) also showed no hemolytic activity against human red blood cells up to 64 μg/mL (highest dose tested). The addition of DNA did not affect the MIC, indicating that the compound of the invention does not bind DNA.

Example 6

In Vivo Efficacy of The Compound of the Invention in a Mouse Septicemia Model

The in vivo efficacy of the compound of Formula (III) was tested in a mouse septicemia model. For the study, six CD-1 female mice were infected with 7.8×10⁷ CFUs of MRSA ATCC 33591 via intraperitoneal injection. At one hour post infection, the mice were intravenously administered the compound of Formula (III) at the doses of 2.5 mg/kg, 5.0 mg/kg, 10.0 mg/kg or 20.0 mg/kg, or vancomycin at the dose of 2.5 mg/kg as a control. Mice that were administered the compound of Formula (III) demonstrated a 50% Protective Dose (PD$_{50}$) value of 5.2 mg/kg. Control mice that were administered vancomycin at a dose of 2.5 mg/kg all survived, as compared to untreated animals which showed only 17% survival.

Example 7

In Vivo Efficacy of the Compound of the Invention in a Mouse Thigh Infection Model The compound of Formula (III) was next evaluated in a neutropenic mouse thigh infection model against *S. aureus* ATCC 33591. For the study, mice challenged with *S. aureus* ATCC 33591 were intravenously administered two 5 mg/kg, 10 mg/kg, 20 mg/kg and 30 mg/kg doses of the compound of Formula (III) at 2 and 4 hours post-infection, or vancomycin as a single dose of 50 mg/kg as a control. The bacterial load in the thigh at 26 hours post-infection was measured.

As shown in FIG. 1, the infection controls demonstrated a bioload of 6.07 log$_{10}$ CFUs/gram of thigh at the time of treatment (2 hours). The 26 hour infection controls demonstrated an increase in bioload of 3.11 log$_{10}$ CFUs from time of treatment. CFU reductions from the 26 hour infection controls were observed at all four studied doses of the compound of Formula (III) in a dose dependent manner. The compound of Formula (III) delivered as two doses of 30 mg/kg 2 hours apart resulted in a 3.59 log$_{10}$ CFU reduction from 26 hour infection controls and a 0.48 log$_{10}$ CFU reduction from the initiation of therapy (T=2 hr). Mice receiving vancomycin demonstrated 0.54 and 3.65 log$_{10}$ CFU reductions from the 2 hour and 26 hour infection controls, respectively.

The results shown in FIG. 1 indicate that the compound of Formula (III) shows good tissue penetration and potential to treat drug-resistant skin infections.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound of the following structural formula:

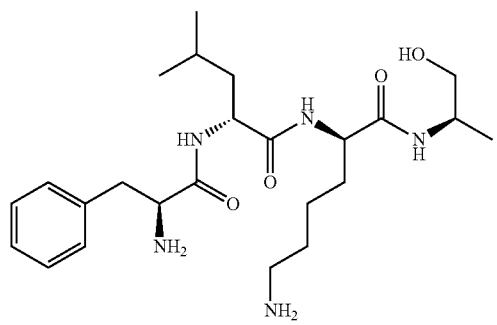

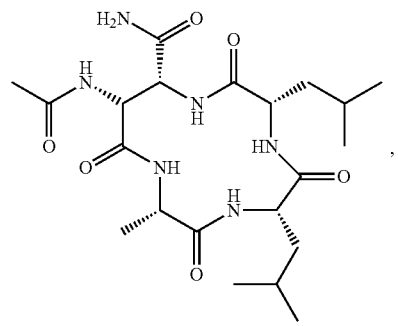

or an enantiomer, diastereomer, tautomer, or pharmaceutically acceptable salt thereof.

2. A pharmaceutical composition comprising the compound of claim 1 and a pharmaceutically acceptable excipient, carrier or diluent.

3. The pharmaceutical composition of claim 2, further comprising an agent selected from the group consisting of an antibiotic, an antifungal agent, an antiviral agent, an antiprotozoan agent, an anthelminthic agent, an anti-neoplastic agent, an immunoregulating agent, an anti-hypercholesterolemia agent and combinations thereof.

4. The pharmaceutical composition of claim 2 comprising a pharmaceutically acceptable carrier that solubilizes the compound.

5. The pharmaceutical composition of claim 2, wherein the pharmaceutically acceptable carrier comprises a sugar, a starch, a cellulose, an oil, a glycol, a polyol, an ester or a buffering agent.

6. The pharmaceutical composition of claim 5, wherein the sugar is selected from the group consisting of lactose, glucose, sucrose and alginic acid.

7. The pharmaceutical composition of claim 5, wherein the start is selected from the group consisting of corn starch and potato starch.

8. The pharmaceutical composition of claim 5, wherein the cellulose is selected from the group consisting of sodium carboxymethyl cellulose, ethyl cellulose, and cellulose acetate.

9. The pharmaceutical composition of claim 5, wherein the oil is selected from the group consisting of peanut oil, cottonseed oil, safflower oil, sesame oil, olive oil, corn oil, and soybean oil.

10. The pharmaceutical composition of claim 5, wherein the polyol is selected from the group consisting of glycerin, sorbitol, mannitol, and polyethylene glycol.

11. A compound of the following structural formula:

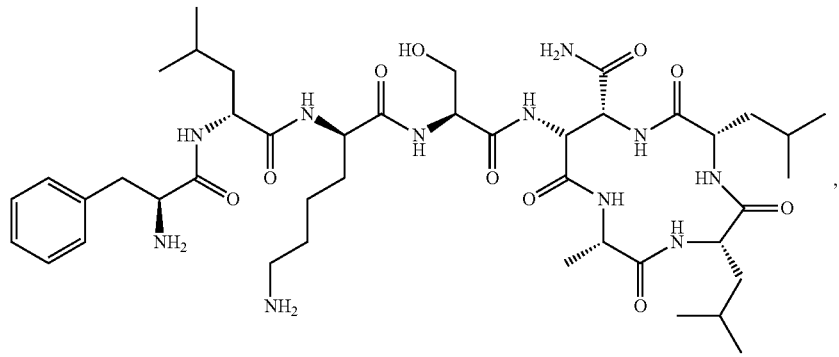

or a pharmaceutically acceptable salt thereof.

12. A pharmaceutical composition comprising the compound of claim 11 and a pharmaceutically acceptable excipient, carrier or diluent.

13. The pharmaceutical composition of claim 12, further comprising an agent selected from the group consisting of an antibiotic, an antifungal agent, an antiviral agent, an anti-protozoan agent, an anthelminthic agent, an anti-neoplastic agent, an immunoregulating agent, an anti-hypercholesterolemia agent and combinations thereof.

14. The pharmaceutical composition of claim 12 comprising a pharmaceutically acceptable carrier that solubilizes the compound.

15. The pharmaceutical composition of claim 12, wherein the pharmaceutically acceptable carrier comprises a sugar, a starch, a cellulose, an oil, a glycol, a polyol, an ester or a buffering agent.

16. The pharmaceutical composition of claim 15, wherein the sugar is selected from the group consisting of lactose, glucose, sucrose and alginic acid.

17. The pharmaceutical composition of claim 15, wherein the start is selected from the group consisting of corn starch and potato starch.

18. The pharmaceutical composition of claim 15, wherein the cellulose is selected from the group consisting of sodium carboxymethyl cellulose, ethyl cellulose, and cellulose acetate.

19. The pharmaceutical composition of claim 15, wherein the oil is selected from the group consisting of peanut oil, cottonseed oil, safflower oil, sesame oil, olive oil, corn oil, and soybean oil.

20. The pharmaceutical composition of claim 15, wherein the polyol is selected from the group consisting of glycerin, sorbitol, mannitol, and polyethylene glycol.

* * * * *